(12) United States Patent  
Vahid et al.

(10) Patent No.: US 7,942,884 B2  
(45) Date of Patent: May 17, 2011

(54) METHODS FOR REDUCTION OF A GASTRIC LUMEN

(75) Inventors: Saadat Vahid, Saratoga, CA (US); Richard C. Ewers, Fullerton, CA (US); Eugene Chen, Carlsbad, CA (US); Rodney Brenneman, San Juan Capistrano, CA (US)

(73) Assignee: USGI Medical, Inc., San Clemente, CA (US)

( * ) Notice: Subject to any disclaimer, the term of this patent is extended or adjusted under 35 U.S.C. 154(b) by 709 days.

(21) Appl. No.: 10/612,491

(22) Filed: Jul. 1, 2003

(65) Prior Publication Data

US 2004/0167546 A1 Aug. 26, 2004

Related U.S. Application Data

(60) Provisional application No. 60/433,065, filed on Dec. 11, 2002.

(51) Int. Cl.
*A61B 17/10* (2006.01)
(52) U.S. Cl. .......... 606/139; 606/213; 606/232
(58) Field of Classification Search ........ 606/153, 606/151, 144, 167, 139, 232–236, 148; 128/898; 446/266, 420–421
See application file for complete search history.

(56) References Cited

U.S. PATENT DOCUMENTS

| | | |
|---|---|---|
| 616,672 A | 12/1898 | Kelling |
| 2,201,610 A | 5/1940 | Dawson, Jr. |
| 2,413,142 A | 12/1945 | Jones et al. |
| 2,510,198 A | 6/1950 | Tesmer |
| 2,533,494 A | 12/1950 | Mitchell, Jr. |
| 3,060,972 A | 10/1962 | Sheldon |
| 3,096,962 A | 7/1963 | Johannes |
| 3,150,379 A | 9/1964 | Brown |
| 3,162,214 A | 12/1964 | Bazinet, Jr. |
| 3,166,072 A | 1/1965 | Sullivan, Jr. |
| 3,168,274 A | 2/1965 | Street |
| 3,190,286 A | 6/1965 | Stokes |
| 3,430,662 A | 3/1969 | Guamaschelli |
| 3,494,006 A | 2/1970 | Brumlik |
| 3,546,961 A | 12/1970 | Marton |
| 3,551,987 A | 1/1971 | Wilkinson |

(Continued)

FOREIGN PATENT DOCUMENTS

EP 0 480 428 A2 4/1992

(Continued)

OTHER PUBLICATIONS

Angiolink, The Expanding Vascular Staple [brochure], 1 page total.

(Continued)

*Primary Examiner* — Todd E Manahan
*Assistant Examiner* — Diane Yabut
(74) *Attorney, Agent, or Firm* — Charles C. Fowler; Levine Bagade Han LLP

(57) ABSTRACT

A method of reducing the cross-sectional area of a gastrointestinal lumen is provided wherein a delivery catheter having a needle, one or more anchors disposed within the needle and a suture coupled to each anchor is advanced into the gastrointestinal lumen, the needle extended through the tissue wall, and an anchor ejected from a distal tip of the needle through the tissue wall. The needle is then repositioned against an opposing tissue wall, another anchor deployed from the needle through the opposing tissue wall, and the tissue walls approximated by applying tension to the sutures.

20 Claims, 10 Drawing Sheets

U.S. PATENT DOCUMENTS

| | | |
|---|---|---|
| 3,646,615 A | 3/1972 | Ness |
| 3,664,345 A | 5/1972 | Dabbs et al. |
| 3,753,438 A | 8/1973 | Wood et al. |
| 3,858,578 A | 1/1975 | Milo |
| 3,867,944 A | 2/1975 | Samuels |
| 3,874,388 A | 4/1975 | King et al. |
| 3,910,281 A | 10/1975 | Kletschka et al. |
| 3,913,565 A | 10/1975 | Kawahara |
| 3,974,834 A | 8/1976 | Kane |
| 3,976,079 A | 8/1976 | Samuels et al. |
| 4,006,747 A | 2/1977 | Kronenthal et al. |
| 4,007,743 A | 2/1977 | Blake |
| 4,036,218 A | 7/1977 | Yamashita et al. |
| 4,054,128 A | 10/1977 | Seufert et al. |
| 4,060,089 A | 11/1977 | Noiles |
| 4,069,825 A | 1/1978 | Akiyama |
| 4,235,238 A | 11/1980 | Ogiu et al. |
| 4,245,624 A | 1/1981 | Komiya |
| 4,366,810 A | 1/1983 | Slanetz |
| 4,367,746 A | 1/1983 | Derechinsky |
| 4,414,720 A | 11/1983 | Crooms |
| 4,462,402 A | 7/1984 | Burgio |
| 4,494,531 A | 1/1985 | Gianturco |
| 4,532,926 A | 8/1985 | O'Holla |
| 4,534,350 A | 8/1985 | Golden et al. |
| 4,548,202 A | 10/1985 | Duncan |
| 4,577,621 A | 3/1986 | Patel |
| 4,586,503 A | 5/1986 | Kirsh et al. |
| 4,592,339 A | 6/1986 | Kumak et al. |
| 4,592,356 A | 6/1986 | Gutierrez |
| 4,595,007 A | 6/1986 | Mericle |
| 4,610,250 A | 9/1986 | Green |
| 4,648,733 A | 3/1987 | Merkt |
| 4,655,257 A | 4/1987 | Iwashita |
| 4,669,473 A | 6/1987 | Richards et al. |
| 4,700,693 A | 10/1987 | Lia et al. |
| 4,705,040 A | 11/1987 | Mueller et al. |
| 4,711,002 A | 12/1987 | Kreeger |
| 4,724,840 A | 2/1988 | McVay et al. |
| 4,750,492 A | 6/1988 | Jacobs et al. |
| 4,765,335 A | 8/1988 | Schmidt et al. |
| 4,790,294 A | 12/1988 | Allred et al. |
| 4,832,055 A | 5/1989 | Palestrant |
| 4,841,888 A | 6/1989 | Mills et al. |
| 4,872,579 A | 10/1989 | Palmer |
| 4,873,976 A | 10/1989 | Schreiber |
| 4,890,615 A | 1/1990 | Caspari et al. |
| 4,923,461 A | 5/1990 | Caspari et al. |
| 4,929,240 A | 5/1990 | Kirsh et al. |
| 4,949,927 A | 8/1990 | Madocks et al. |
| 4,957,498 A | 9/1990 | Caspari et al. |
| 5,005,558 A | 4/1991 | Aomori |
| 5,025,778 A | 6/1991 | Silverstein et al. |
| 5,032,127 A | 7/1991 | Frazee et al. |
| 5,035,692 A | 7/1991 | Lyon et al. |
| 5,037,433 A | 8/1991 | Wilk et al. |
| 5,041,129 A | 8/1991 | Hayhurst et al. |
| 5,059,201 A | 10/1991 | Asnis |
| 5,068,719 A | 11/1991 | Tsuji |
| 5,073,166 A | 12/1991 | Parks et al. |
| 5,088,979 A | 2/1992 | Filipi et al. |
| 5,100,418 A | 3/1992 | Yoon et al. |
| 5,108,420 A | 4/1992 | Marks |
| 5,122,136 A | 6/1992 | Gugliemi et al. |
| 5,123,914 A | 6/1992 | Cope |
| RE34,021 E | 8/1992 | Mueller et al. |
| 5,174,276 A | 12/1992 | Crockard |
| 5,176,691 A | 1/1993 | Pierce |
| 5,179,935 A | 1/1993 | Miyagi |
| 5,201,746 A | 4/1993 | Shichman |
| 5,203,864 A | 4/1993 | Phillips |
| 5,217,471 A | 6/1993 | Burkhart |
| 5,217,473 A | 6/1993 | Yoon |
| 5,222,508 A | 6/1993 | Contarini |
| 5,222,961 A | 6/1993 | Nakao et al. |
| 5,222,963 A | 6/1993 | Brinkerhoff et al. |
| 5,224,946 A | 7/1993 | Hayhurst et al. |
| 5,234,430 A | 8/1993 | Huebner |
| 5,234,445 A | 8/1993 | Walker et al. |
| 5,250,053 A | 10/1993 | Snyder |
| 5,251,611 A | 10/1993 | Zehel et al. |
| 5,254,126 A | 10/1993 | Filipi et al. |
| 5,261,916 A | 11/1993 | Engelson |
| 5,268,001 A | 12/1993 | Nicholson et al. |
| 5,269,809 A | 12/1993 | Hayhurst et al. |
| 5,271,381 A | 12/1993 | Ailinger et al. |
| 5,282,827 A | 2/1994 | Kensey et al. |
| 5,284,488 A | 2/1994 | Sideris |
| 5,289,817 A | 3/1994 | Williams et al. |
| 5,304,184 A | 4/1994 | Hathaway et al. |
| 5,304,195 A | 4/1994 | Twyford, Jr. et al. |
| 5,304,204 A | 4/1994 | Bregen |
| 5,316,543 A | 5/1994 | Eberbach |
| 5,327,914 A | 7/1994 | Shlain |
| 5,330,503 A | 7/1994 | Yoon |
| 5,334,217 A | 8/1994 | Das |
| 5,337,732 A | 8/1994 | Grundfest et al. |
| 5,337,733 A | 8/1994 | Bauerfeind et al. |
| 5,342,376 A | 8/1994 | Ruff |
| 5,345,949 A | 9/1994 | Shlain |
| 5,348,259 A | 9/1994 | Blanco et al. |
| 5,350,399 A | 9/1994 | Erlebacher et al. |
| 5,354,298 A | 10/1994 | Lee et al. |
| 5,366,459 A | 11/1994 | Yoon |
| 5,366,479 A | 11/1994 | McGarry et al. |
| 5,372,146 A | 12/1994 | Branch |
| 5,372,604 A | 12/1994 | Trott |
| 5,374,275 A | 12/1994 | Bradley et al. |
| 5,380,334 A | 1/1995 | Torrie et al. |
| 5,382,231 A | 1/1995 | Shlain |
| 5,395,030 A | 3/1995 | Kuramoto et al. |
| 5,403,326 A | 4/1995 | Harrison et al. |
| 5,403,329 A | 4/1995 | Hinchcliffe |
| 5,417,691 A | 5/1995 | Hayhurst et al. |
| 5,417,699 A | 5/1995 | Klein et al. |
| 5,425,744 A | 6/1995 | Fagan et al. |
| 5,429,598 A | 7/1995 | Waxman et al. |
| 5,431,666 A | 7/1995 | Sauer et al. |
| 5,433,721 A | 7/1995 | Hooven et al. |
| 5,433,727 A | 7/1995 | Sideris |
| 5,437,266 A | 8/1995 | McPherson et al. |
| 5,437,680 A | 8/1995 | Yoon |
| 5,437,681 A | 8/1995 | Meade et al. |
| 5,445,167 A | 8/1995 | Yoon et al. |
| 5,451,235 A | 9/1995 | Lock et al. |
| 5,458,609 A | 10/1995 | Gordon et al. |
| 5,462,560 A | 10/1995 | Stevens |
| 5,462,561 A | 10/1995 | Voda |
| 5,465,894 A | 11/1995 | Clark et al. |
| 5,470,337 A | 11/1995 | Moss |
| 5,470,338 A | 11/1995 | Whitfield et al. |
| 5,476,470 A | 12/1995 | Fitzgibbons, Jr. |
| 5,478,354 A | 12/1995 | Tovey et al. |
| 5,480,405 A | 1/1996 | Yoon |
| 5,496,332 A | 3/1996 | Sierra et al. |
| 5,496,334 A | 3/1996 | Klundt et al. |
| 5,499,991 A | 3/1996 | Garman et al. |
| 5,501,691 A | 3/1996 | Goldrath |
| 5,507,811 A | 4/1996 | Koike et al. |
| 5,520,691 A | 5/1996 | Branch |
| 5,520,701 A | 5/1996 | Lerch |
| 5,522,843 A | 6/1996 | Zang |
| 5,527,321 A | 6/1996 | Hinchliffe |
| 5,527,322 A | 6/1996 | Klein et al. |
| 5,527,342 A | 6/1996 | Pietrzak et al. |
| 5,531,759 A | 7/1996 | Kensey et al. |
| 5,531,788 A | 7/1996 | Dibie et al. |
| 5,540,704 A | 7/1996 | Gordon et al. |
| 5,545,178 A | 8/1996 | Kensey et al. |
| 5,549,618 A | 8/1996 | Fleenor et al. |
| 5,549,621 A | 8/1996 | Bessler et al. |
| 5,558,665 A | 9/1996 | Kieturakis |
| 5,562,684 A | 10/1996 | Kammerer |
| 5,562,686 A | 10/1996 | Sauer et al. |
| 5,562,688 A | 10/1996 | Riza |
| 5,569,274 A | 10/1996 | Rapacki et al. |
| 5,569,306 A | 10/1996 | Thal |

| | | | | | | |
|---|---|---|---|---|---|---|
| 5,571,116 A | 11/1996 | Bolanos et al. | | 5,817,107 A | 10/1998 | Schaller |
| 5,571,119 A | 11/1996 | Atala | | 5,817,110 A | 10/1998 | Kronner |
| 5,573,496 A | 11/1996 | McPherson et al. | | 5,823,956 A | 10/1998 | Roth et al. |
| 5,573,540 A | 11/1996 | Yoon | | 5,824,011 A | 10/1998 | Stone et al. |
| 5,573,548 A | 11/1996 | Nazre et al. | | 5,827,298 A | 10/1998 | Hart et al. |
| 5,575,801 A | 11/1996 | Habermeyer et al. | | 5,829,447 A | 11/1998 | Stevens et al. |
| 5,578,045 A | 11/1996 | Das | | 5,836,955 A | 11/1998 | Buelna et al. |
| 5,582,616 A | 12/1996 | Bolduc et al. | | 5,840,078 A | 11/1998 | Yerys |
| 5,584,835 A | 12/1996 | Greenfield | | 5,843,084 A | 12/1998 | Hart et al. |
| 5,584,859 A | 12/1996 | Brotz | | 5,843,126 A | 12/1998 | Jameel |
| 5,591,186 A | 1/1997 | Wurster et al. | | 5,846,261 A | 12/1998 | Kotula et al. |
| 5,601,557 A | 2/1997 | Hayhurst | | 5,855,614 A | 1/1999 | Stevens et al. |
| 5,603,718 A | 2/1997 | Xu | | 5,860,991 A | 1/1999 | Klein et al. |
| 5,613,974 A | 3/1997 | Andreas et al. | | 5,861,003 A | 1/1999 | Latson et al. |
| 5,613,975 A | 3/1997 | Christy | | 5,865,791 A | 2/1999 | Whayne et al. |
| 5,624,381 A | 4/1997 | Kieturakis | | 5,868,760 A | 2/1999 | McGuckin |
| 5,626,588 A | 5/1997 | Sauer et al. | | 5,868,762 A | 2/1999 | Cragg et al. |
| 5,626,614 A | 5/1997 | Hart | | 5,879,371 A | 3/1999 | Gardiner et al. |
| 5,630,540 A | 5/1997 | Blewett | | 5,887,594 A | 3/1999 | LoCiero, III |
| 5,632,752 A | 5/1997 | Buelna | | 5,888,247 A | 3/1999 | Benetti |
| 5,643,274 A | 7/1997 | Sander et al. | | 5,891,168 A | 4/1999 | Thal |
| 5,643,295 A | 7/1997 | Yoon | | 5,893,856 A | 4/1999 | Jacobs et al. |
| 5,643,317 A | 7/1997 | Pavcnik et al. | | 5,895,404 A | 4/1999 | Ruiz |
| 5,643,320 A | 7/1997 | Lower et al. | | 5,897,417 A | 4/1999 | Grey |
| 5,653,038 A | 8/1997 | Hunter | | 5,897,562 A | 4/1999 | Bolanos et al. |
| 5,658,312 A | 8/1997 | Green et al. | | 5,899,920 A | 5/1999 | DeSatnick et al. |
| 5,658,313 A | 8/1997 | Thal | | 5,899,921 A | 5/1999 | Caspari et al. |
| 5,662,587 A | 9/1997 | Grundfest et al. | | 5,901,895 A | 5/1999 | Heaton et al. |
| 5,662,654 A | 9/1997 | Thompson | | 5,902,254 A | 5/1999 | Magram |
| 5,662,662 A | 9/1997 | Bishop et al. | | 5,916,147 A | 6/1999 | Boury |
| 5,662,663 A | 9/1997 | Shallman | | 5,916,224 A | 6/1999 | Esplin |
| 5,665,109 A | 9/1997 | Yoon | | 5,921,915 A | 7/1999 | Aznoian et al. |
| 5,665,112 A | 9/1997 | Thal | | 5,925,059 A | 7/1999 | Palermo et al. |
| 5,667,513 A | 9/1997 | Torrie et al. | | 5,928,260 A | 7/1999 | Chin et al. |
| 5,669,917 A | 9/1997 | Sauer et al. | | 5,928,264 A | 7/1999 | Sugarbaker et al. |
| 5,676,670 A | 10/1997 | Kim | | 5,935,107 A | 8/1999 | Taylor et al. |
| 5,676,674 A | 10/1997 | Bolanos et al. | | 5,941,815 A | 8/1999 | Chang |
| 5,679,005 A | 10/1997 | Einstein | | 5,944,738 A | 8/1999 | Amplatz et al. |
| 5,683,417 A | 11/1997 | Cooper | | 5,947,983 A | 9/1999 | Solar et al. |
| 5,683,419 A | 11/1997 | Thal | | 5,947,997 A | 9/1999 | Pavcnik et al. |
| 5,690,655 A | 11/1997 | Hart et al. | | 5,948,001 A | 9/1999 | Larsen |
| 5,693,060 A | 12/1997 | Martin | | 5,954,731 A | 9/1999 | Yoon |
| 5,700,273 A | 12/1997 | Buelna et al. | | 5,954,732 A | 9/1999 | Hart et al. |
| 5,702,397 A | 12/1997 | Goble et al. | | 5,961,440 A | 10/1999 | Schweich, Jr. et al. |
| 5,702,419 A | 12/1997 | Berry et al. | | 5,964,765 A | 10/1999 | Fenton, Jr. et al. |
| 5,702,421 A | 12/1997 | Schneidt | | 5,964,782 A | 10/1999 | Lafontaine et al. |
| 5,707,394 A | 1/1998 | Miller et al. | | 5,964,783 A | 10/1999 | Grafton et al. |
| 5,709,707 A | 1/1998 | Lock et al. | | 5,971,933 A | 10/1999 | Gopakumaran et al. |
| 5,709,708 A | 1/1998 | Thal | | 5,976,073 A | 11/1999 | Ouchi |
| 5,713,903 A | 2/1998 | Sander et al. | | 5,976,127 A | 11/1999 | Lax |
| 5,720,765 A | 2/1998 | Thal | | 5,976,158 A | 11/1999 | Adams et al. |
| 5,724,978 A | 3/1998 | Tenhoff | | 5,976,159 A | 11/1999 | Bolduc et al. |
| 5,725,552 A | 3/1998 | Kotula et al. | | 5,980,558 A | 11/1999 | Wiley |
| 5,728,045 A | 3/1998 | Komi | | 5,984,933 A | 11/1999 | Yoon |
| 5,732,707 A | 3/1998 | Widder et al. | | 5,993,476 A | 11/1999 | Groiso |
| 5,741,297 A | 4/1998 | Simon | | 6,013,083 A | 1/2000 | Bennett |
| 5,746,752 A | 5/1998 | Burkhart | | 6,017,358 A | 1/2000 | Yoon et al. |
| 5,746,755 A | 5/1998 | Wood et al. | | 6,027,523 A | 2/2000 | Schmieding |
| 5,749,828 A | 5/1998 | Solomon et al. | | 6,033,430 A | 3/2000 | Bonutti |
| 5,749,893 A | 5/1998 | Vidal et al. | | 6,036,699 A | 3/2000 | Andreas et al. |
| 5,752,963 A | 5/1998 | Allard et al. | | 6,042,155 A | 3/2000 | Lockwood |
| 5,759,151 A | 6/1998 | Sturges | | 6,045,497 A | 4/2000 | Schweich, Jr. et al. |
| 5,766,189 A | 6/1998 | Matsuno | | 6,045,573 A | 4/2000 | Wenstrom, Jr. et al. |
| 5,769,816 A | 6/1998 | Barbut et al. | | 6,050,936 A | 4/2000 | Schweich, Jr. et al. |
| 5,776,150 A | 7/1998 | Nolan et al. | | 6,053,935 A | 4/2000 | Brenneman et al. |
| 5,779,719 A | 7/1998 | Klein et al. | | 6,056,760 A * | 5/2000 | Koike et al. .................. 606/148 |
| 5,782,859 A | 7/1998 | Nicholas et al. | | 6,056,770 A | 5/2000 | Epstein et al. |
| 5,782,865 A | 7/1998 | Grotz | | 6,059,715 A | 5/2000 | Schweich, Jr. et al. |
| 5,787,897 A | 8/1998 | Kieturakis | | 6,059,719 A | 5/2000 | Yamamoto et al. |
| 5,792,152 A | 8/1998 | Klein et al. | | 6,074,401 A | 6/2000 | Gardiner et al. |
| 5,792,153 A | 8/1998 | Swain et al. | | 6,077,214 A | 6/2000 | Mortier et al. |
| 5,797,929 A | 8/1998 | Andreas et al. | | 6,077,281 A | 6/2000 | Das |
| 5,797,960 A | 8/1998 | Stevens et al. | | 6,077,291 A | 6/2000 | Das |
| 5,810,849 A | 9/1998 | Kontos | | 6,079,414 A | 6/2000 | Roth et al. |
| 5,810,851 A | 9/1998 | Yoon | | 6,086,600 A | 7/2000 | Kortenbach |
| 5,810,853 A | 9/1998 | Yoon | | 6,086,601 A | 7/2000 | Yoon |
| 5,810,882 A | 9/1998 | Bolduc et al. | | 6,110,183 A | 8/2000 | Cope |
| 5,814,064 A | 9/1998 | Daniel et al. | | 6,113,609 A | 9/2000 | Adams |
| 5,814,070 A | 9/1998 | Borzone et al. | | 6,113,611 A | 9/2000 | Allen et al. |

| | | | | | | |
|---|---|---|---|---|---|---|
| 6,119,913 | A | 9/2000 | Adams et al. | 6,699,263 B2 | 3/2004 | Cope |
| 6,149,658 | A | 11/2000 | Gardiner et al. | 6,702,826 B2 | 3/2004 | Liddicoat et al. |
| 6,152,935 | A | 11/2000 | Kammerer et al. | 6,716,232 B1 | 4/2004 | Vidal et al. |
| 6,152,946 | A | 11/2000 | Broome et al. | 6,719,763 B2 | 4/2004 | Chung et al. |
| 6,159,146 | A | 12/2000 | El Gazayerli | 6,719,764 B1 | 4/2004 | Gellman et al. |
| 6,162,168 | A | 12/2000 | Schweich, Jr. et al. | 6,736,828 B1 * | 5/2004 | Adams et al. .................. 606/213 |
| 6,165,119 | A | 12/2000 | Schweich, Jr. et al. | 6,746,460 B2 * | 6/2004 | Gannoe et al. .................. 606/153 |
| 6,165,120 | A | 12/2000 | Schweich, Jr. et al. | 6,755,843 B2 | 6/2004 | Chung et al. |
| 6,167,889 | B1 | 1/2001 | Benetti | 6,761,685 B2 | 7/2004 | Adams et al. |
| 6,171,320 | B1 | 1/2001 | Monassevitch | 6,773,440 B2 | 8/2004 | Gannoe et al. |
| 6,174,323 | B1 | 1/2001 | Biggs et al. | 6,773,441 B1 | 8/2004 | Laufer et al. |
| 6,179,195 | B1 | 1/2001 | Adams et al. | 6,800,056 B2 | 10/2004 | Tartaglia et al. |
| 6,179,776 | B1 | 1/2001 | Adams et al. | 6,811,532 B2 | 11/2004 | Ogura et al. |
| 6,183,411 | B1 | 2/2001 | Mortier et al. | 6,821,285 B2 | 11/2004 | Laufer et al. |
| RE37,117 | E | 3/2001 | Palermo | 6,835,199 B2 * | 12/2004 | McGuckin et al. ........... 606/142 |
| 6,197,022 | B1 | 3/2001 | Baker | 6,837,846 B2 | 1/2005 | Jaffe et al. |
| 6,214,007 | B1 | 4/2001 | Anderson | 6,837,849 B2 | 1/2005 | Ogura et al. |
| 6,214,028 | B1 | 4/2001 | Yoon et al. | 6,921,378 B2 | 7/2005 | O'Keefe et al. |
| 6,221,084 | B1 | 4/2001 | Fleenor | 6,932,834 B2 | 8/2005 | Lizardi et al. |
| 6,228,023 | B1 | 5/2001 | Zaslavsky et al. | 6,955,657 B1 | 10/2005 | Webler |
| 6,231,561 | B1 | 5/2001 | Frazier et al. | 6,986,781 B1 | 1/2006 | Smith |
| 6,238,412 | B1 | 5/2001 | Dubrul et al. | 6,994,717 B2 | 2/2006 | Kónya et al. |
| 6,245,079 | B1 | 6/2001 | Nobles et al. | 6,997,931 B2 | 2/2006 | Sauer et al. |
| 6,260,552 | B1 | 7/2001 | Mortier et al. | 7,063,630 B2 | 6/2006 | Cavallaro |
| 6,261,222 | B1 | 7/2001 | Schweich, Jr. et al. | 7,083,630 B2 | 8/2006 | DeVries et al. |
| 6,264,602 | B1 | 7/2001 | Mortier et al. | 7,131,980 B1 | 11/2006 | Field et al. |
| 6,270,515 | B1 | 8/2001 | Linden et al. | 7,160,312 B2 | 1/2007 | Saadat |
| 6,283,973 | B1 | 9/2001 | Hubbard et al. | 7,186,262 B2 * | 3/2007 | Saadat .......................... 606/232 |
| 6,287,315 | B1 | 9/2001 | Wijeratne et al. | 7,416,554 B2 | 8/2008 | Lam et al. |
| 6,290,674 | B1 | 9/2001 | Roue et al. | 2001/0000040 A1 | 3/2001 | Adams et al. |
| 6,293,956 | B1 | 9/2001 | Crainich et al. | 2001/0016675 A1 | 8/2001 | Mortier et al. |
| 6,296,656 | B1 | 10/2001 | Bolduc et al. | 2001/0025171 A1 | 9/2001 | Mortier et al. |
| 6,306,159 | B1 | 10/2001 | Schwartz et al. | 2001/0049509 A1 | 12/2001 | Sekine et al. |
| 6,306,163 | B1 | 10/2001 | Fitz | 2001/0051815 A1 | 12/2001 | Esplin |
| 6,312,437 | B1 | 11/2001 | Kortenbach | 2001/0056282 A1 | 12/2001 | Sonnenschein et al. |
| 6,315,789 | B1 | 11/2001 | Cragg | 2002/0010490 A1 | 1/2002 | Schaller et al. |
| 6,322,563 | B1 | 11/2001 | Cummings et al. | 2002/0013608 A1 | 1/2002 | ElAttrache et al. |
| 6,322,580 | B1 | 11/2001 | Kanner | 2002/0019649 A1 | 2/2002 | Sikora et al. |
| 6,332,468 | B1 | 12/2001 | Benetti | 2002/0022851 A1 | 2/2002 | Kalloo et al. |
| 6,332,863 | B1 | 12/2001 | Schweich, Jr. et al. | 2002/0029080 A1 | 3/2002 | Mortier et al. |
| 6,332,864 | B1 | 12/2001 | Schweich, Jr. et al. | 2002/0040226 A1 | 4/2002 | Laufer et al. |
| 6,332,893 | B1 | 12/2001 | Mortier et al. | 2002/0049458 A1 | 4/2002 | Singhatat |
| 6,336,940 | B1 | 1/2002 | Graf et al. | 2002/0055689 A1 | 5/2002 | Kaplan et al. |
| 6,346,074 | B1 | 2/2002 | Roth | 2002/0055757 A1 | 5/2002 | Torre et al. |
| 6,348,064 | B1 | 2/2002 | Kanner | 2002/0058855 A1 | 5/2002 | Schweich, Jr. et al. |
| 6,352,503 | B1 * | 3/2002 | Matsui et al. .................. 600/104 | 2002/0058905 A1 | 5/2002 | Madrid et al. |
| 6,355,052 | B1 | 3/2002 | Neuss et al. | 2002/0062062 A1 | 5/2002 | Belson et al. |
| 6,358,197 | B1 | 3/2002 | Silverman et al. | 2002/0065534 A1 | 5/2002 | Hermann et al. |
| 6,363,938 | B2 | 4/2002 | Saadat et al. | 2002/0068849 A1 | 6/2002 | Schweich, Jr. et al. |
| 6,368,338 | B1 | 4/2002 | Kónya et al. | 2002/0068945 A1 | 6/2002 | Sixto, Jr. et al. |
| 6,368,339 | B1 | 4/2002 | Amplatz et al. | 2002/0072761 A1 | 6/2002 | Abrams et al. |
| 6,387,104 | B1 | 5/2002 | Pugsley, Jr. | 2002/0077524 A1 | 6/2002 | Schweich, Jr. et al. |
| 6,391,044 | B1 | 5/2002 | Yadav et al. | 2002/0078967 A1 | 6/2002 | Sixto, Jr. et al. |
| 6,402,679 | B1 | 6/2002 | Mortier et al. | 2002/0082621 A1 | 6/2002 | Schurr et al. |
| 6,402,680 | B2 | 6/2002 | Mortier et al. | 2002/0082622 A1 | 6/2002 | Kane |
| 6,406,420 | B1 | 6/2002 | McCarthy et al. | 2002/0087098 A1 | 7/2002 | Iwami et al. |
| H2037 | H | 7/2002 | Yates et al. | 2002/0107530 A1 | 8/2002 | Sauer et al. |
| 6,423,087 | B1 | 7/2002 | Sawada | 2002/0111534 A1 | 8/2002 | Suzuki et al. |
| 6,425,859 | B1 | 7/2002 | Foley et al. | 2002/0116012 A1 | 8/2002 | May et al. |
| 6,425,911 | B1 | 7/2002 | Akerfeldt et al. | 2002/0120178 A1 | 8/2002 | Tartaglia et al. |
| 6,447,533 | B1 | 9/2002 | Adams et al. | 2002/0147385 A1 | 10/2002 | Butler et al. |
| 6,494,888 | B1 | 12/2002 | Laufer et al. | 2002/0161281 A1 | 10/2002 | Jaffe et al. |
| 6,506,190 | B1 * | 1/2003 | Walshe .......................... 606/139 | 2002/0183768 A1 | 12/2002 | Deem et al. |
| 6,506,196 | B1 | 1/2003 | Laufer | 2002/0193661 A1 | 12/2002 | Belson |
| 6,508,828 | B1 | 1/2003 | Akerfeldt et al. | 2002/0193662 A1 | 12/2002 | Belson |
| 6,533,796 | B1 | 3/2003 | Sauer et al. | 2002/0193816 A1 | 12/2002 | Laufer et al. |
| 6,537,285 | B1 | 3/2003 | Hatasaka, Jr. et al. | 2002/0198537 A1 | 12/2002 | Smith et al. |
| 6,554,793 | B1 | 4/2003 | Pauker et al. | 2003/0009085 A1 | 1/2003 | Arai et al. |
| 6,554,845 | B1 | 4/2003 | Fleenor et al. | 2003/0024205 A1 | 2/2003 | Strickland |
| 6,558,400 | B2 | 5/2003 | Deem et al. | 2003/0045778 A1 | 3/2003 | Ohline et al. |
| 6,572,629 | B2 | 6/2003 | Kalloo et al. | 2003/0055442 A1 | 3/2003 | Laufer et al. |
| 6,589,208 | B2 | 7/2003 | Ewers et al. | 2003/0065359 A1 | 4/2003 | Weller et al. |
| 6,592,596 | B1 | 7/2003 | Geitz | 2003/0109892 A1 | 6/2003 | Deem et al. |
| 6,641,592 | B1 | 11/2003 | Sauer et al. | 2003/0109900 A1 | 6/2003 | Martinek |
| 6,656,182 | B1 | 12/2003 | Hayhurst | 2003/0120289 A1 | 6/2003 | McGuckin et al. |
| 6,656,194 | B1 | 12/2003 | Gannoe et al. | 2003/0139752 A1 | 7/2003 | Pasricha et al. |
| 6,663,639 | B1 | 12/2003 | Laufer et al. | 2003/0158582 A1 | 8/2003 | Bonutti et al. |
| 6,669,707 | B1 | 12/2003 | Swanstrom et al. | 2003/0165887 A1 | 9/2003 | Reed |
| 6,695,764 | B2 | 2/2004 | Silverman et al. | 2003/0167062 A1 | 9/2003 | Gambale et al. |

| | | |
|---|---|---|
| 2003/0167071 A1 | 9/2003 | Martin et al. |
| 2003/0171651 A1 | 9/2003 | Page et al. |
| 2003/0171760 A1 | 9/2003 | Gambale |
| 2003/0176890 A1 | 9/2003 | Buckman et al. |
| 2003/0181924 A1 | 9/2003 | Yamamoto et al. |
| 2003/0204205 A1 | 10/2003 | Sauer et al. |
| 2003/0240205 | 10/2003 | Sauer et al. |
| 2003/0208209 A1 | 11/2003 | Gambale et al. |
| 2003/0208211 A1 | 11/2003 | Kortenbach |
| 2003/0216613 A1 | 11/2003 | Suzuki et al. |
| 2003/0225312 A1 | 12/2003 | Suzuki et al. |
| 2003/0229296 A1 | 12/2003 | Ishikawa et al. |
| 2003/0236505 A1 | 12/2003 | Bonadio et al. |
| 2003/0236536 A1 | 12/2003 | Grigoryants et al. |
| 2004/0010271 A1 | 1/2004 | Kortenbach |
| 2004/0030347 A1 | 2/2004 | Gannoe et al. |
| 2004/0049095 A1 | 3/2004 | Goto et al. |
| 2004/0059346 A1 | 3/2004 | Adams et al. |
| 2004/0082963 A1 | 4/2004 | Gannoe et al. |
| 2004/0088008 A1 | 5/2004 | Gannoe et al. |
| 2004/0092974 A1 | 5/2004 | Gannoe et al. |
| 2004/0093091 A1 | 5/2004 | Gannoe et al. |
| 2004/0097986 A1 | 5/2004 | Adams |
| 2004/0116949 A1 | 6/2004 | Ewers et al. |
| 2004/0122452 A1 | 6/2004 | Deem et al. |
| 2004/0122453 A1 | 6/2004 | Deem et al. |
| 2004/0122456 A1 | 6/2004 | Saadat et al. |
| 2004/0122473 A1 | 6/2004 | Ewers et al. |
| 2004/0122474 A1 | 6/2004 | Gellman et al. |
| 2004/0133238 A1 | 7/2004 | Cerier |
| 2004/0138682 A1 | 7/2004 | Onuki et al. |
| 2004/0147941 A1 | 7/2004 | Takemoto |
| 2004/0147958 A1 | 7/2004 | Lam et al. |
| 2004/0162568 A1 | 8/2004 | Saadat et al. |
| 2004/0167546 A1 | 8/2004 | Saadat et al. |
| 2004/0176784 A1 | 9/2004 | Okada |
| 2004/0193008 A1 | 9/2004 | Jaffe et al. |
| 2004/0193009 A1 | 9/2004 | Jaffe et al. |
| 2004/0193117 A1 | 9/2004 | Laufer et al. |
| 2004/0193184 A1 | 9/2004 | Laufer et al. |
| 2004/0193193 A1 | 9/2004 | Laufer et al. |
| 2004/0193194 A1 | 9/2004 | Laufer et al. |
| 2004/0194790 A1* | 10/2004 | Laufer et al. .................. 128/898 |
| 2004/0210243 A1 | 10/2004 | Gannoe et al. |
| 2004/0215216 A1 | 10/2004 | Gannoe et al. |
| 2004/0225183 A1 | 11/2004 | Michlitsch et al. |
| 2004/0225305 A1 | 11/2004 | Ewers et al. |
| 2004/0243152 A1 | 12/2004 | Taylor et al. |
| 2004/0249362 A1 | 12/2004 | Levine et al. |
| 2004/0249367 A1 | 12/2004 | Saadat et al. |
| 2004/0249392 A1 | 12/2004 | Mikkaichi et al. |
| 2004/0249395 A1 | 12/2004 | Mikkaichi et al. |
| 2005/0004576 A1 | 1/2005 | Benderev |
| 2005/0020901 A1 | 1/2005 | Belson et al. |
| 2005/0033320 A1 | 2/2005 | McGuckin, Jr. et al. |
| 2005/0033328 A1 | 2/2005 | Laufer et al. |
| 2005/0043758 A1 | 2/2005 | Golden et al. |
| 2005/0049617 A1 | 3/2005 | Chatlynne et al. |
| 2005/0065397 A1 | 3/2005 | Saadat et al. |
| 2005/0065401 A1 | 3/2005 | Saadat et al. |
| 2005/0065536 A1 | 3/2005 | Ewers et al. |
| 2005/0070931 A1 | 3/2005 | Li et al. |
| 2005/0075653 A1 | 4/2005 | Saadat et al. |
| 2005/0113640 A1 | 5/2005 | Saadat et al. |
| 2005/0119671 A1 | 6/2005 | Reydel et al. |
| 2005/0149115 A1 | 7/2005 | Roue et al. |
| 2005/0192629 A1 | 9/2005 | Saadat et al. |
| 2005/0203488 A1 | 9/2005 | Michlitsch et al. |
| 2005/0203500 A1 | 9/2005 | Saadat et al. |
| 2005/1020348 | 9/2005 | Saadat at al. |
| 2005/0234294 A1 | 10/2005 | Saadat et al. |
| 2005/0234296 A1 | 10/2005 | Saadat et al. |
| 2005/0250980 A1 | 11/2005 | Swanstrom et al. |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0251091 A1 | 11/2005 | Saadat et al. |
| 2005/0251157 A1 | 11/2005 | Saadat et al. |
| 2005/0251158 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251165 A1 | 11/2005 | Vaughan et al. |
| 2005/0251166 A1 | 11/2005 | Vaughan et al. |
| 2005/0251176 A1 | 11/2005 | Swanstrom et al. |
| 2005/0251177 A1 | 11/2005 | Saadat et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251209 A1 | 11/2005 | Saadat et al. |
| 2005/0251210 A1 | 11/2005 | Westra et al. |
| 2005/1024594 | 11/2005 | Ewers at al. |
| 2005/1025098 | 11/2005 | Rothe at al. |
| 2005/0267523 A1 | 12/2005 | Devellian et al. |
| 2005/0272977 A1 | 12/2005 | Saadat et al. |
| 2005/0273135 A1 | 12/2005 | Chanduszko et al. |
| 2005/0277945 A1 | 12/2005 | Saadat et al. |
| 2005/0277966 A1 | 12/2005 | Ewers et al. |
| 2005/0277975 A1 | 12/2005 | Saadat et al. |
| 2005/0277981 A1 | 12/2005 | Maahs et al. |
| 2005/0277983 A1 | 12/2005 | Saadat et al. |
| 2006/0009789 A1 | 1/2006 | Gambale et al. |
| 2006/0020274 A1 | 1/2006 | Ewers et al. |
| 2006/0020276 A1 | 1/2006 | Saadat et al. |
| 2006/0100579 A1 | 5/2006 | Maahs et al. |
| 2006/0135971 A1 | 6/2006 | Swanstrom et al. |
| 2006/0161185 A1 | 7/2006 | Saadat et al. |
| 2006/1015706 | 7/2006 | Saadat et al. |
| 2006/0178560 A1 | 8/2006 | Saadat et al. |
| 2006/0178562 A1 | 8/2006 | Saadat et al. |
| 2006/0183975 A1 | 8/2006 | Saadat et al. |
| 2006/0184161 A1 | 8/2006 | Maahs et al. |
| 2006/0189845 A1 | 8/2006 | Maahs et al. |

FOREIGN PATENT DOCUMENTS

| | | |
|---|---|---|
| EP | 0 847 727 A1 | 6/1998 |
| EP | 1 031 321 A1 | 8/2000 |
| FR | 2 768 324 A1 | 3/1999 |
| GB | 2 165 559 A | 4/1986 |
| WO | WO 92/04870 A1 | 4/1992 |
| WO | WO 95/19140 A1 | 7/1995 |
| WO | WO 95/25468 A1 | 9/1995 |
| WO | WO 99/22649 A2 | 5/1999 |
| WO | WO 00/40159 A1 | 7/2000 |
| WO | WO 00/57796 A1 | 10/2000 |
| WO | WO 00/78227 A1 | 12/2000 |
| WO | WO 00/78229 A1 | 12/2000 |
| WO | WO 01/21246 A1 | 3/2001 |
| WO | WO 01/66001 A2 | 9/2001 |
| WO | WO 01/66018 A1 | 9/2001 |
| WO | WO 01/85034 A1 | 11/2001 |
| WO | WO 01/87144 A1 | 11/2001 |
| WO | WO 01/89370 A2 | 11/2001 |
| WO | WO 01/89392 A2 | 11/2001 |
| WO | WO 01/89393 A1 | 11/2001 |
| WO | WO 02/00119 A2 | 1/2002 |
| WO | WO 02/24080 A2 | 3/2002 |
| WO | WO 02/30335 | 4/2002 |
| WO | WO 02/39880 A2 | 5/2002 |
| WO | WO 02/060328 A1 | 8/2002 |
| WO | WO 02/064012 A2 | 8/2002 |
| WO | WO 02/085252 A1 | 10/2002 |
| WO | WO 02/094105 A2 | 11/2002 |
| WO | WO 03/007796 A2 | 1/2003 |
| WO | WO 03/007799 A2 | 1/2003 |
| WO | WO 03/090633 A2 | 11/2003 |
| WO | WO 03/092509 A1 | 11/2003 |
| WO | WO 03/094785 A1 | 11/2003 |
| WO | WO 03/096909 A2 | 11/2003 |
| WO | WO 03/099137 A2 | 12/2003 |
| WO | WO 03/105732 A1 | 12/2003 |
| WO | WO 2004/004542 A2 | 1/2004 |
| WO | WO 2004/004544 A2 | 1/2004 |
| WO | WO 2004/019787 A2 | 3/2004 |

| | | |
|---|---|---|
| WO | WO 2004/019788 A2 | 3/2004 |
| WO | WO 2004/021865 A2 | 3/2004 |
| WO | WO 2004/021867 A2 | 3/2004 |
| WO | WO 2004/021868 A2 | 3/2004 |
| WO | WO 2004/021873 A2 | 3/2004 |
| WO | WO 2004/021894 A1 | 3/2004 |
| WO | WO 2004/056273 A1 | 7/2004 |
| WO | WO 2004/075787 A1 | 9/2004 |
| WO | WO 2004/084808 A2 | 10/2004 |
| WO | WO 2004/103189 A1 | 12/2004 |
| WO | WO 2005/004727 A1 | 1/2005 |
| WO | WO 2005/037072 A2 | 4/2005 |
| WO | WO 2005/037152 A1 | 4/2005 |

OTHER PUBLICATIONS

Bluett et al., "Experimental Evaluation of Staple Lines in Gastric Surgery," *Arch. Surg.*, vol. 122, (Jul. 1987), pp. 772-776.

Brolin et al., Experimental Evaluation of Techniques of Gastric Paritioning for Morbid Obesity, Surgery, Gynecology & Obstetrics, vol. 153, (Dec. 1981), pp. 878-882.

Johnston et al. "The Magenstrasse and Mill Operation of Morbid Obesity", *Obesity Surgery* 13, (2003), pp. 10-16.

Okudaira et al., "The Healing and Tensile Strength of the Gastroplasty Staple Line," *The American Surgeon*, (Oct. 1984), pp. 564-568.

Surgical Dynamics Inc., The S•D•sorb Meniscal Stapler [brochure] (1997), 3 pages total.

Sutura, The Next Generation in Vascular Suturing Devices: SuperStitch [brochure], 2 pages total.

Chuttani et al., "A Novel Endoscopic Full-thickness Plicator for Treatment of GERD: An Animal Model Study," *Gastrointestinal Endoscopy*, vol. 26, No. 1,( 2002), pp. 116-122.

Mason, "Development of Future of Gastroplasties for Morbid Obesity," *Arch Surg*, vol. 138 (Apr. 2003), pp. 362-366.

Bluett et al., "Experimental Evaluation of Staple Lines in Gastric Surgery," *Arch. Surg.*, vol. 122, Jul. 1987, pp. 772-776.

File History for U.S. Appl. No. 10/612,109 filed Jul. 1, 2003.
File History for U.S. Appl. No. 10/612,170 filed Jul. 1, 2003.
File History for U.S. Appl. No. 10/639,162 filed Aug. 12, 2003.
File History for U.S. Appl. No. 10/672,375 filed Sep. 25, 2003.
File History for U.S. Appl. No. 10/992,912 filed Nov. 18, 2004.
File History for U.S. Appl. No. 10/734,547 filed Dec. 12, 2003.
File History for U.S. Appl. No. 10/734,562 filed Dec. 12, 2003
File History for U.S. Appl. No. 10/735,030 filed Dec. 12, 2003.
File History for U.S. Appl. No. 10/992,306 tiled Nov. 17, 2004.
File History for U.S. Appl. No. 10/994,101 filed Nov. 18, 2004.
File History for European Patent Application No, 3817830.7 filed Dec. 22, 2003.

European Patent Application No. 3817830.7 filed Dec. 22, 2003, Supplemental European Search Report mailed Oct. 19, 2009.

PCT International Patent Application No. PCT/US2003/040859 filed Dec. 22, 2003, International Search Report mailed Jun. 22, 2005.

PCT International Patent Application No. PCT/US2003/034726 flied Oct. 31, 2003, International Search Report mailed Jan. 21, 2005.

PCT International Patent Application No. PCTIUS2004/041570 filed Dec. 10, 2004, International Search Report mailed Oct. 4, 2005.

PCT International Patent Application No. PCT/US2004/041570 filed Dec. 10, 2004, International Preliminary Report on Patentability mailed Jun. 12, 2006.

\* cited by examiner

METHODS FOR REDUCTION OF A GASTRIC LUMEN

REFERENCE TO RELATED APPLICATIONS

This application claims priority from U.S. Provisional Patent Application No. 60/433,065, filed Dec. 11, 2002, which is incorporated herein by reference in its entirety.

FIELD OF THE INVENTION

The present invention relates to methods and apparatus for reducing the effective cross-sectional area of a gastro-intestinal ("GI") lumen.

BACKGROUND OF THE INVENTION

Morbid obesity is a serious medical condition pervasive in the United States and other countries. Its complications include hypertension, diabetes, coronary artery disease, stroke, congestive heart failure, multiple orthopedic problems and pulmonary insufficiency with markedly decreased life expectancy.

Several surgical techniques have been developed to treat morbid obesity, e.g., bypassing an absorptive surface of the small intestine, or reducing the stomach size. These procedures are difficult to perform in morbidly obese patients because it is often difficult to gain access to the digestive organs. In particular, the layers of fat encountered in morbidly obese patients make difficult direct exposure of the digestive organs with a wound retractor, and standard laparoscopic trocars may be of inadequate length.

In addition, previously known open surgical procedures may present numerous life-threatening post-operative complications, and may cause a typical diarrhea, electrolytic imbalance, unpredictable weight loss and reflux of nutritious chyme proximal to the site of the anastamosis. Further, the sutures or staples that are often used in these surgical procedures may require extensive training by the clinician to achieve competent use, and may concentrate significant force over a small surface area of the tissue, thereby potentially causing the suture or staple to tear through the tissue.

In view of the aforementioned limitations, it would be desirable to provide methods and apparatus for achieving gastric reduction by reconfiguring the GI lumen of a patient.

It also would be desirable to provide methods for delivering anchors for use in a gastric reduction system for reducing the cross-sectional area of a gastrointestinal lumen.

It further would be desirable to provide methods for reducing the cross-sectional area of a gastrointestinal lumen by approximating opposing tissue walls of the gastrointestinal lumen.

It further would be desirable to provide methods and apparatus for creating gastrointestinal tissue folds to facilitate tissue approximation within a gastrointestinal lumen.

SUMMARY OF THE INVENTION

In view of the foregoing, it is an object of the present invention to provide methods and apparatus for achieving gastric reduction by approximating tissue to reconfigure the GI lumen of a patient.

It is another object of the present invention to provide methods for delivering anchors for use in a gastric reduction system for reducing the cross-sectional area of a gastrointestinal lumen.

It is an additional object of this invention to provide methods for reducing the cross-sectional area of a gastrointestinal lumen by approximating opposing tissue walls of the gastrointestinal lumen.

It is a further object of the present invention to provide methods and apparatus for creating gastrointestinal tissue folds to facilitate tissue approximation within a gastrointestinal lumen.

These and other aspects of the present invention are accomplished by providing a gastric reduction system including methods and apparatus for delivering a plurality of anchors on opposing sides of a gastro-intestinal lumen and then moving the anchors to approximate the opposing walls of the lumen. In accordance with the principles of the present invention, the anchors may have any of a variety of configurations employing radially expanding sleeves or struts.

One aspect of the present invention involves a method of delivering an anchor for use in a gastric reduction system for reducing the cross-sectional area of a gastrointestinal lumen. A preliminary step involves providing a delivery catheter including a needle translatably disposed therein, a stabilization device attached to a distal end of the delivery catheter and one or more anchors disposed within the needle. Subsequent steps include advancing the delivery into the gastrointestinal lumen, attaching the stabilization device to a tissue wall of the gastrointestinal lumen, pushing the needle through the tissue wall and ejecting an anchor from a distal tip of the needle. The method may further include the steps of providing an endoscope translatably disposed within the delivery catheter to provide visual guidance during anchor delivery.

Another aspect of the present invention involves a method of reducing the cross-sectional area of a gastrointestinal lumen. A preliminary step involves providing a delivery catheter including a needle translatably disposed therein, one or more anchors disposed within the needle and a suture coupled to each anchor. Subsequent steps include advancing the delivery catheter into the gastrointestinal lumen, pushing the needle through the tissue wall, ejecting an anchor from a distal tip of the needle through the tissue wall, pushing the needle through an opposing tissue wall, ejecting an anchor from a distal tip of the needle through the opposing tissue wall and approximating the tissue walls by applying tension to the sutures.

The method may further include the steps of providing a stabilization device disposed from a distal end of the delivery catheter and engaging the stabilization device to the tissue wall before pushing the needle through the tissue wall. According to some embodiments, the stabilization device comprises a coil that is screwed into the tissue wall to stabilize the tissue during anchor delivery. Additionally, the step of approximating the tissue walls may include the steps of providing a fastener for maintaining tension in the sutures, threading the sutures through the fastener and crimping the fastener to maintain the tension in the sutures. The method may further include the step of cutting unneeded lengths of the sutures.

A further aspect of the present invention involves a method of creating a gastrointestinal tissue fold including the preliminary step of providing a delivery catheter including a translatable curved needle, an anchor disposed within the needle and a suture coupled to the anchor. Subsequent steps involve pushing the needle through the tissue wall at a first location such that the needle curves around and punctures the tissue wall at a second location, ejecting the anchor from the curved needle and tensioning the suture to create the tissue fold. The method may also include the steps of providing a second anchor including a suture coupled thereto, creating a second tissue fold on an opposing tissue wall and approximating the tissue folds by applying tension to the sutures.

An additional aspect of the present invention involves a method of creating a gastrointestinal tissue fold including the preliminary step of providing a delivery catheter including a translatable needle, a jaw assembly, an anchor disposed within the needle and a suture coupled to the anchor. Subsequent steps involve grabbing and pulling a tissue wall of the gastrointestinal lumen using the jaw assembly to create a tissue fold, pushing the needle through the tissue fold, ejecting the anchor from the needle and maintaining the tissue fold by applying tension to the suture.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
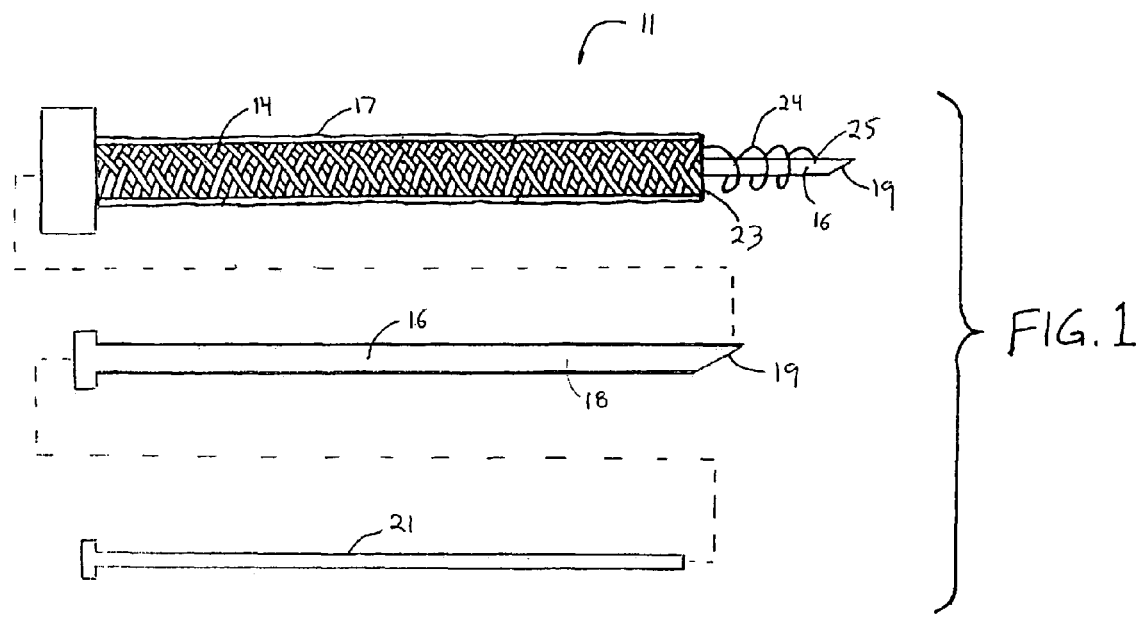
FIG. 1 is a schematic view of an illustrative delivery catheter for use with the gastric reduction methods of the present invention.

Overview of a Preferred Gastric Reduction System

Referring to FIGS. 1-7, illustrative components of gastric reduction apparatus 10 in accordance with the principles of the present invention are described. As explained in detail hereinafter, apparatus 10 enables a clinician to treat obesity by approximating the walls of a gastro-intestinal lumen to narrow the lumen, thus reducing the area for absorption in the stomach or intestines. Gastric reduction system 10 comprises anchor delivery catheter 11, anchor 22, and optionally, suture tensioning assembly 50. The structure and operation of each of these components are described separately below.

A. Delivery Catheter

Figure 2:
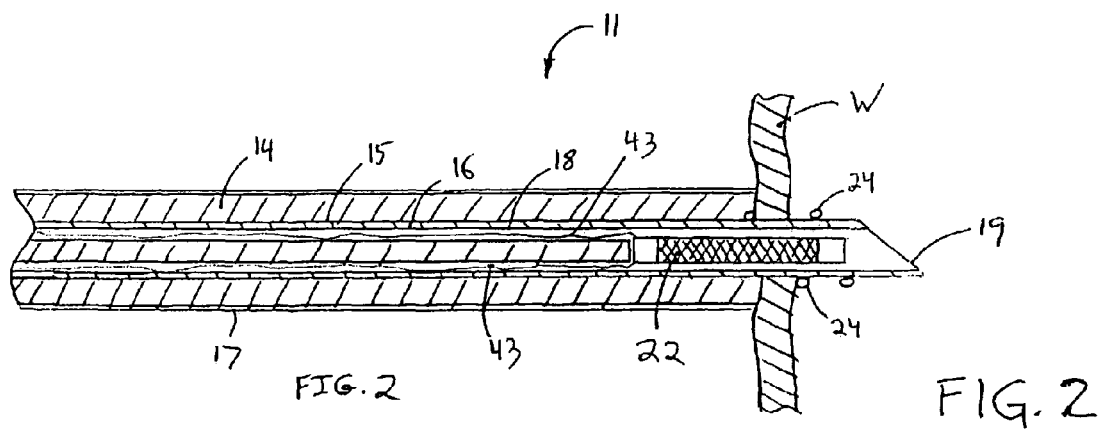
FIG. 2 is a side-sectional view of the delivery catheter of FIG. 1, loaded with an anchor of the present invention, penetrating a GI tissue wall of a patient.

Referring now to FIGS. 1 and 2, an illustrative embodiment of delivery catheter 11 constructed in accordance with the principles of the present invention is described. Delivery catheter 11 comprises elongate torqueable tube 14 having lumen 15 and needle 16 disposed for translation within lumen 15. Torqueable tube 14 preferably is formed of braided stainless steel wire having TEFLON coating 17. Needle 16 includes lumen 18 and non-coring distal tip 19 that facilitates penetration of tissue wall W. Needle 16 preferably is configured to penetrate tissue wall W so that the tissue anchor, described below, may employ a substantially atraumatic distal tip.

Push rod 21 is disposed for translation within lumen 18, and is configured to eject anchor 22 (see FIG. 2) out of distal end 23 of the delivery catheter and through tissue wall W. As shown in FIG. 2, one or more sutures 43 are attached to anchor 22, and extend through lumen 18 of needle 16 so that the proximal ends of the sutures 43 extend out of the mouth of the patient.

To facilitate penetration of needle 16 into tissue wall W, delivery catheter 11 preferably includes a stabilization device in the form of coil 24 that may be engaged to tissue wall W to stabilize distal end 23 of delivery catheter 11 against the tissue during actuation of needle 16. Coil 24 preferably is attached at one end to distal end 23 of catheter 11 and terminates at the other end in sharpened tip 25. According to some embodiments, coil 24 and needle are coaxial such that coil 24 defines a central passage that permits needle 16 to be reciprocated therethrough.

Figure 3:
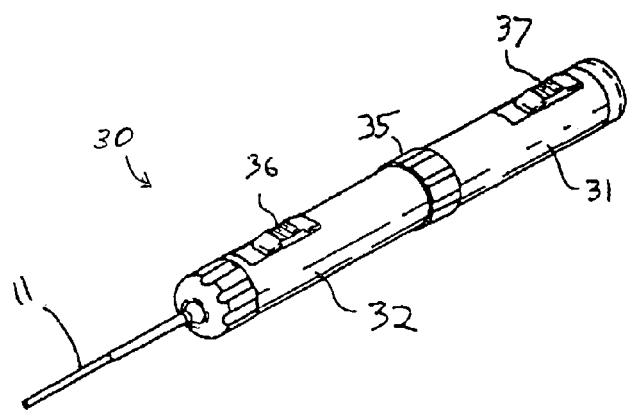
FIG. 3 is a perspective view of the handle of the catheter of FIGS. 1 and 2.

Referring to FIG. 3, an illustrative handle 30 for controlling operation of delivery catheter 11 is described. Handle 30 comprises proximal portion 31 and distal portion 32. Distal portion 32 is coupled to elongate tube 14 so that rotation of knob 35 rotates coil 24 to engage wall W of the gastrointestinal tissue, as illustrated in FIG. 2. Handle 30 further comprises slider buttons 36 and 37 for imparting translational movement to needle 16 and push rod 21, respectively.

In operation, after knob 35 has been rotated to engage coil 24 to tissue wall W, slider button 36 is actuated to urge needle 16 distally to pass through coil 24 and penetrate wall W. Once needle tip 19 has penetrated the tissue wall, slider button 37 is actuated urge push rod 21 distally, thus ejecting anchor 22 from needle 16 on the distal side of tissue wall W. After the anchor assembly has been deployed, slider buttons 36 and 37 are retracted in the proximal direction to retract the needle and push rod back within elongate tube 14. Knob 35 may then be rotated in the opposite direction to release its engagement with tissue wall W.

B. Anchor

Figure 4A:
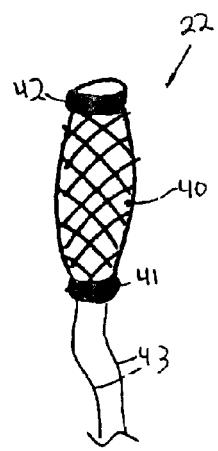
FIGS. 4A and 4B are views of one preferred embodiment of an anchor of the present invention in the reduced delivery state.
Figure 4B:
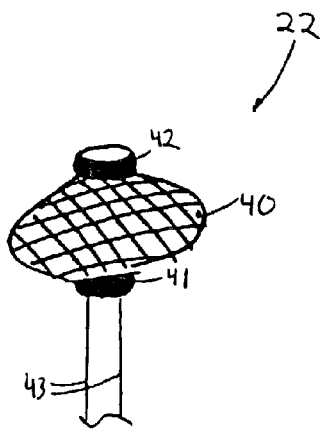

Referring now to FIGS. 4A and 4B, a preferred embodiment of anchor 22 constructed in accordance with the principles of the present invention is described. Anchor 22 comprises braided sleeve 40 coupled to proximal bushing 41 and distal bushing 42. One or more sutures 43 are coupled to distal bushing 42 and extend through bushing 41. Proximal bushing 41 may slide along the suture(s) relative to the distal bushing 42, so that braided sleeve expands radially outward. Accordingly, after anchor 22 is disposed through a tissue wall (as depicted in FIG. 2), application of tension to the sutures causes the anchor to transition from an elongate reduced delivery profile (FIG. 4a) to an expanded, substantially disk-shaped deployed profile (FIG. 4B).

Braided sleeve 40 preferably comprises a highly porous, compliant and high strength material composed of numerous individual monofilament elements. Suitable materials for the monofilament elements include polyester, nylon, TEFLON, polypropylene and combinations thereof. Braided sleeve 40 also may be formed from a shape memory metal, such as a Nickel-Titanium alloy. In addition, the porous braid structure may promote an easily and uniformly absorbable structure for use in applications in which anchor 22 is not intended for permanent implantation. Conversely, the porous braid structure may promote tissue growth to enhance anchoring in applications in which anchor 22 is designed for permanent implantation.

Anchor 22 may be made by thermo-forming two ends of a short length of braided sleeve to form proximal and distal bushings 41 and 42. Alternatively, separate bushings may be glued, over-molded, soldered or welded onto the ends of a length of braided sleeve. Suture(s) 43 may be attached to distal bushing 42 at a fixture point comprising, for example, one or more holes 46 formed in the distal bushing. Alternatively, the sutures may be attached using an eyelet, adhesive or other suitable fastener.

Figure 5A:
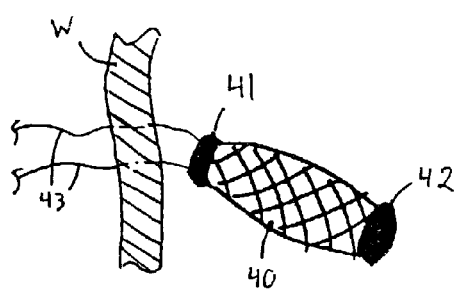
FIGS. 5A-5C are side views depicting transmural implantation of the anchor assembly of FIGS. 4A-4B.
Figure 5B:
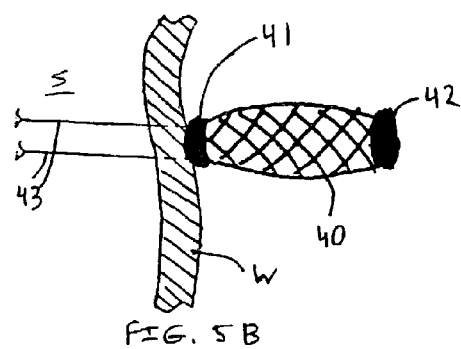
Figure 5C:
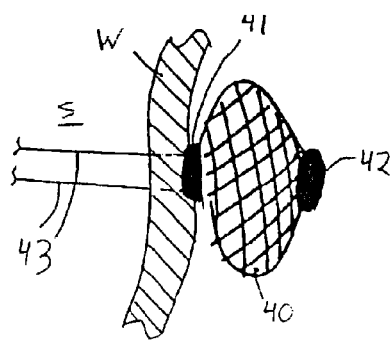

FIGS. 5A-5C depict deployment of anchor 22 from the reduced delivery profile to the expanded deployed profile. In FIG. 5A, anchor 22 has been forced through tissue wall W, illustratively the stomach wall, via needle lumen 18. Once delivery catheter 11 is withdrawn, anchor 22 is left disposed through tissue wall W with untensioned sutures 43 extending into the patient's stomach S. Sutures 43 pass through the esophagus and extend from the patient's mouth where they may be manipulated by the clinician.

In FIG. 5B, sutures 43 are shown partially tensioned, so that proximal bushing 41 engages the distal surface of tissue wall W. Because the stomach wall comprises a tough, resilient material, contact between the expanded braided sleeve and distal surface of the tissue wall causes the braided sleeve to partially expand, rather than slip back into the stomach vua the track left by needle 16. When further tension is applied to sutures 43, distal bushing 42 is approximated toward proximal bushing 41, thereby causing braided sleeve 40 to expand in the radially to the substantially disk-shaped profile shown in FIG. 5C.

Alternatively, anchor 22 may be preformed to self-expand to disk-shaped profile to automatically upon ejection from lumen 18 of needle 16. Such a preset shape may be accomplished by coupling the anchor to a fixture (e.g., a mandrel) and heat setting the braided sleeve in the disk-shaped profile. For example, the bushings may be approximated and then retained in close proximity by a fixture, or the shape may be imposed by compressing the braid in a disk-shaped mold. The formed anchor and fixture then may be placed into an oven for a predetermined amount of time, and quenched or slowly cooled to room temperature.

C. Suture Tensioning Assembly

Figure 6:
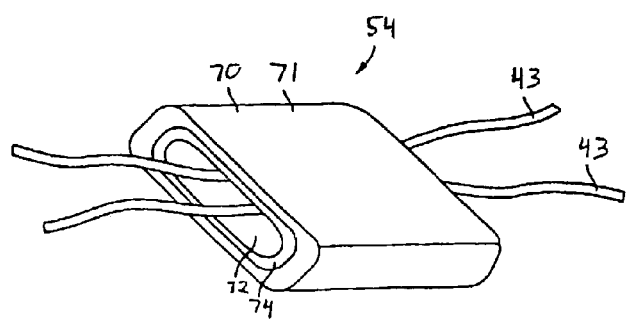
FIG. 6 is a perspective view of a fastener suitable for use with the anchors of the present invention.

Referring now to FIG. 6, illustrative suture fastener 54 constructed in accordance with the principles of the present invention is described. Fastener 54 comprises collar 70 having body 71 and channel 72 through which sutures 43 may freely translate prior to crimping. Once fastener 54 is crimped, sutures 43 are restrained from further translation through channel 72, thus retaining a desired amount of tension on sutures 43. Optionally, body 71 may incorporate lining 74 to enhance friction between body 71 and suture 43, thereby reducing the risk of slippage.

Figure 7A:
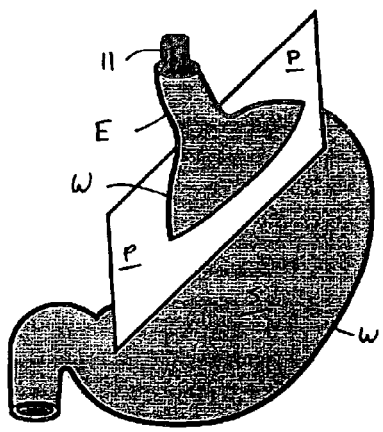
FIGS. 7A-7E are cross-sectional views depicting methods of using the gastric reduction system of the present invention.

FIGS. 7A to 7E illustrate the steps of one procedure using gastric reduction system 10 to treat obesity. In FIG. 7A delivery catheter 11 of FIGS. 1-3 is inserted through a patient's mouth, esophagus E and stomach S. FIGS. 7B-7E depict cross-sectional views of the stomach taken along plane P of FIG. 7A.

Figure 7B:
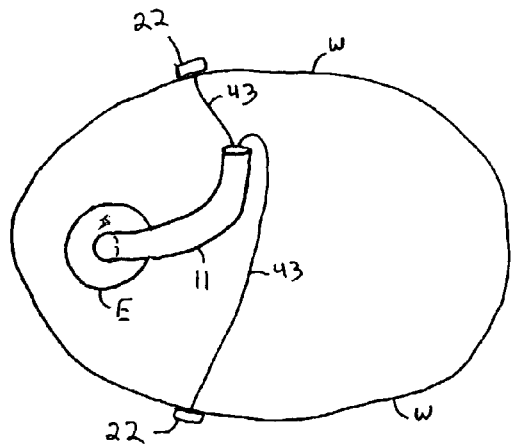
Figure 7C:
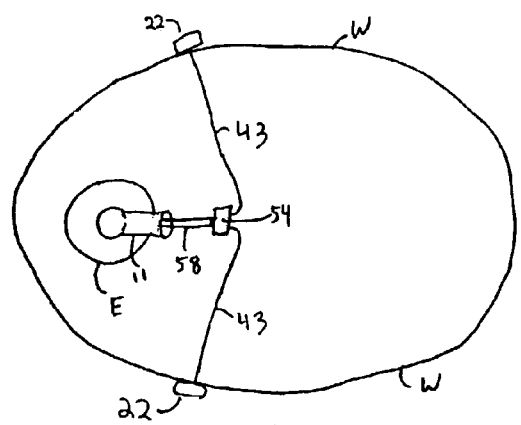

FIG. 7B depicts a step in the which a pair of anchors 22 have been positioned through opposing tissue walls W of the stomach so that sutures 43 pass from each anchor through esophagus E and extend out of the patient's mouth. FIG. 7C depicts a step in which sutures 43 have been threaded through the channel of fastener 54. At this point, fastener 54 has not been crimped and may be freely translated along sutures 43 using a push rod. More particularly, tension is maintained in the sutures while push rod 58 is used to urge fastener 54 through patient's mouth and esophagus E and into the stomach.

Figure 7D:
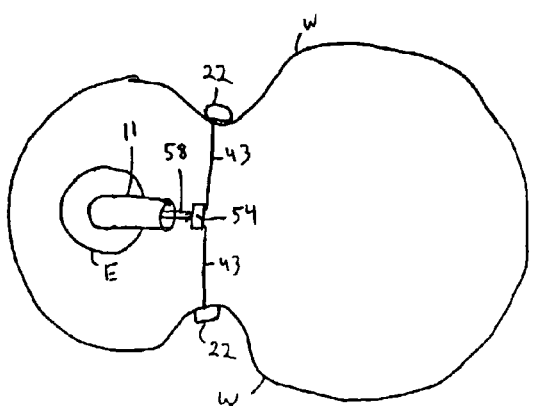
Figure 7E:
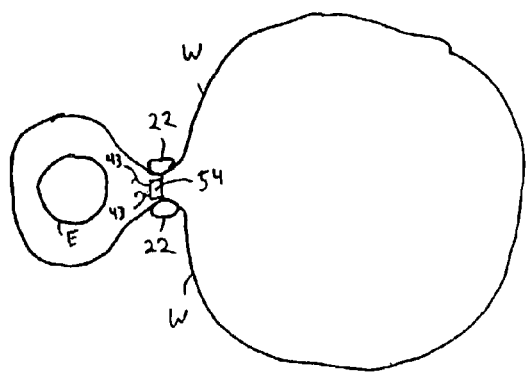

FIG. 7D depicts a step in which fastener 54 is moved to a position approximately midway between anchors 22. Push rod 58 then is used to hold the fastener in place while additional tension is applied to the sutures, thereby causing opposing walls W of the stomach to bow inward toward one another. As depicted in FIG. 7E, the application of additional tension pulls the opposing tissue walls into proximity with each other, thereby narrowing the cross-sectional area of stomach S.

At this step in the procedure, fastener 54 is crimped to maintain the tension in sutures 43. The excess length of sutures 43 is cut and removed via the patient's mouth. Advantageously, narrowing of stomach S limits the amount of food the patient consumes by providing a feeling of satiety after only a small amount of food is ingested.

Alternatively or in addition, sutures 43 may comprise self-tightening materials that shrink over time, or materials such as nickel titanium or electroactive polymers that are pre-stretched so that the subsequent application of heat or electricity causes the sutures to shorten. By way of example, if pre-stretched nickel titanium or electroactive polymeric sutures are used, heat from a radiofrequency device or hot water may be used after the procedure to induce the sutures to tighten. Tension may be controlled by the ability of the sutures to tighten to a specific load. Tension also may be maintained by tying a knot or fusing the sutures to each other via application of heat.

Method of Stomach Reduction Using the Gastric Reduction System

Figure 8A:
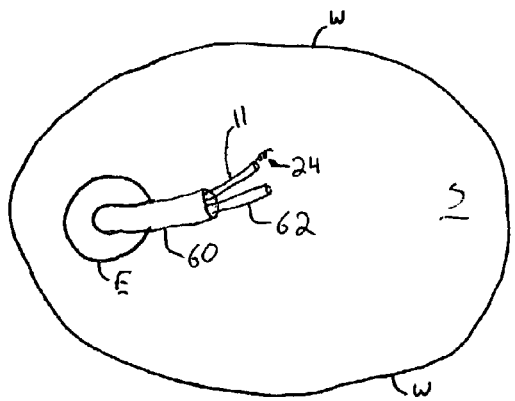
FIGS. 8A-8H are cross-sectional views depicting a preferred method of using the gastric reduction system of the present invention.

FIGS. 8A to 8E are cross-sectional views of a patient's stomach S that illustrate a preferred method of using gastric reduction system 10. FIG. 8A depicts a step in which guide catheter 60 is advanced through esophagus E and disposed in a proximal portion of stomach S. Next, endoscope 62 is advanced through the guide catheter and delivery catheter is positioned within stomach S under the visual guidance provided by endoscope 62.

Referring again to FIGS. 1-3, delivery catheter 11 includes needle 16 translatably disposed within lumen 15, one or more anchors 22 translatably disposed within needle 16, coil 24 for stabilizing the distal end 23 of delivery catheter 11 against tissue wall W during anchor delivery, push rod 21 configured to eject anchor 22 out of distal end 23 of the delivery catheter and through tissue wall W, and one or more sutures 43 are attached to anchor 22.

Figure 8B:
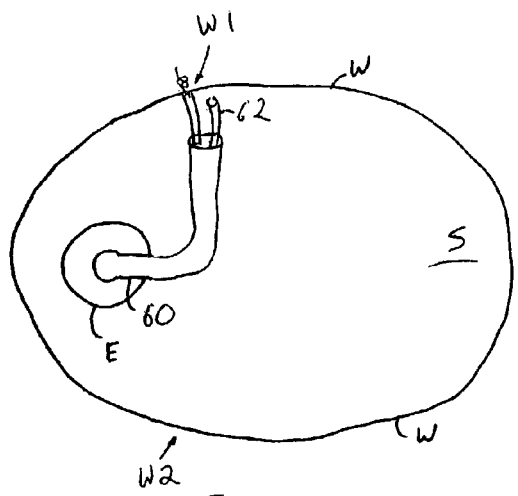
Figure 8C:
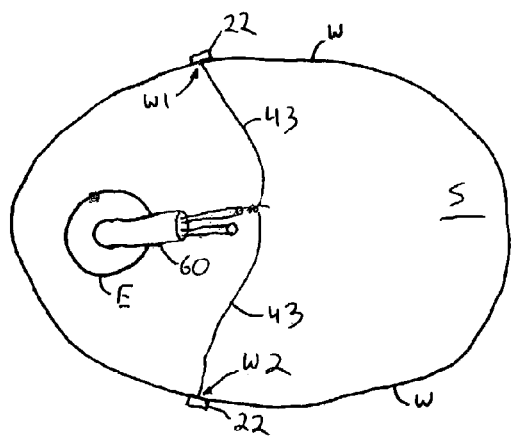

FIG. 8B depicts a step in which coil 24 is screwed into tissue wall W at a first location W1. Coil 24 is used to stabilize the delivery catheter during anchor delivery. Referring again to FIG. 2, after coil is screwed into the tissue wall, needle 16 is translated distally within delivery catheter 11 such that distal tip 19 travels through tissue wall W. In the next step, push rod 21 is used to eject anchor 22 from distal tip 19 and through tissue wall W. Then, coil 24 is screwed into tissue wall W at a second location W2 and the above-described anchor delivery steps are repeated. Referring to FIG. 8C, after anchor delivery, a suture 43 extends from each anchor 22, through delivery catheter 11, and out of the mouth of the patient.

Figure 8D:
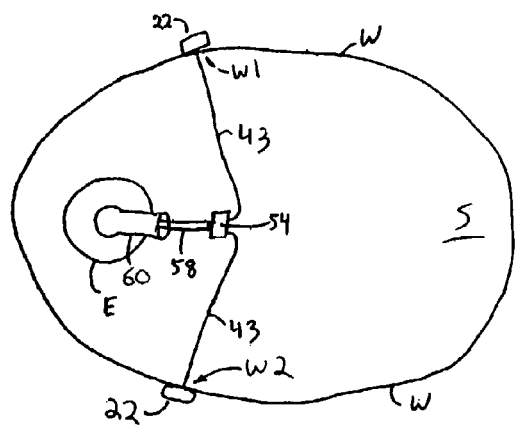

FIG. 8D depicts a step in which sutures 43 have been threaded through the channel of fastener 54. At this point, fastener 54 has not been crimped such that sutures 43 may be freely translated within the fastener channel using push rod 58. Tension is maintained in the sutures while push rod 58 is used to urge fastener 54 through esophagus E and into the stomach S.

Figure 8E:
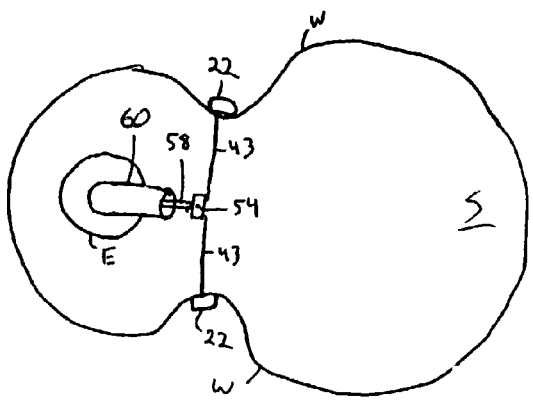
Figure 8F:
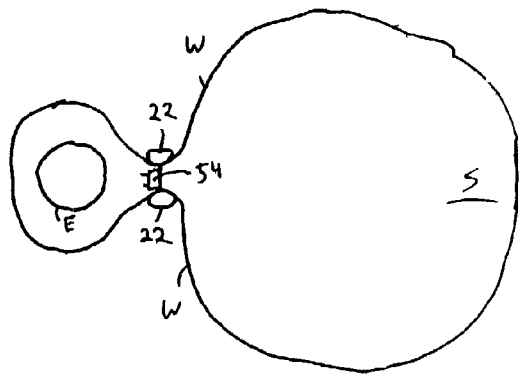

FIG. 8E depicts a step in which fastener 54 is moved to a position approximately midway between anchors 22. Push rod 58 then is used to hold the fastener in place while additional tension is applied to the sutures, thereby causing opposing walls W of the stomach to bow inward toward one another. FIG. 8F depicts a step in which the application of additional tension to sutures 43 pulls the opposing tissue walls into proximity with each other, thereby narrowing the cross-sectional area of stomach S.

Figure 8G:
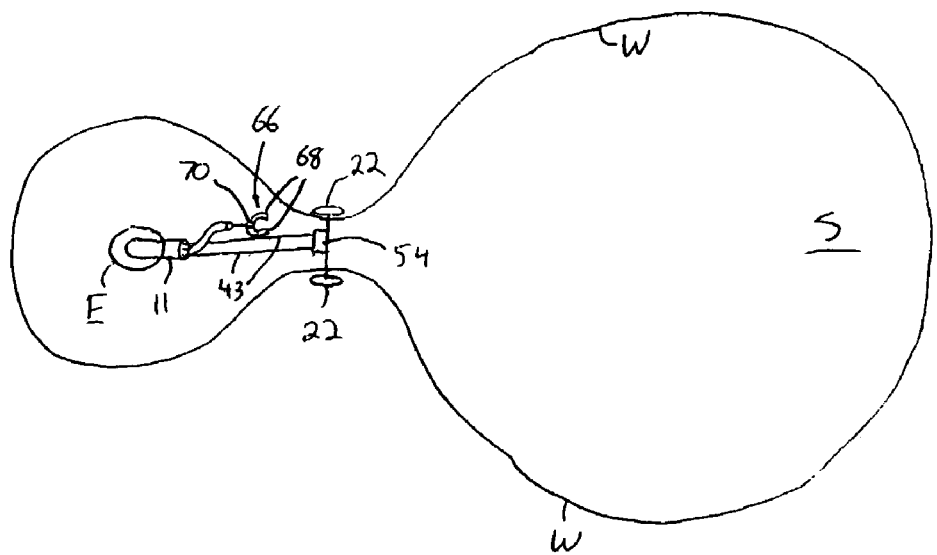

FIG. 8G depicts a step in which a pliers assembly 66 is used to crimp fastener 54 and thereby retain sutures 43 under tension. Pliers assembly 66 comprises arms 68 arranged to articulate about pivot point 70. Pliers assembly 66 is used to grip and crimp fastener 54 by manipulating an actuator disposed generally at the proximal end of catheter 11. After crimping fastener 54, pliers assembly 66 is retracted and scissor assembly 72 is advanced through catheter 11.

Figure 8H:
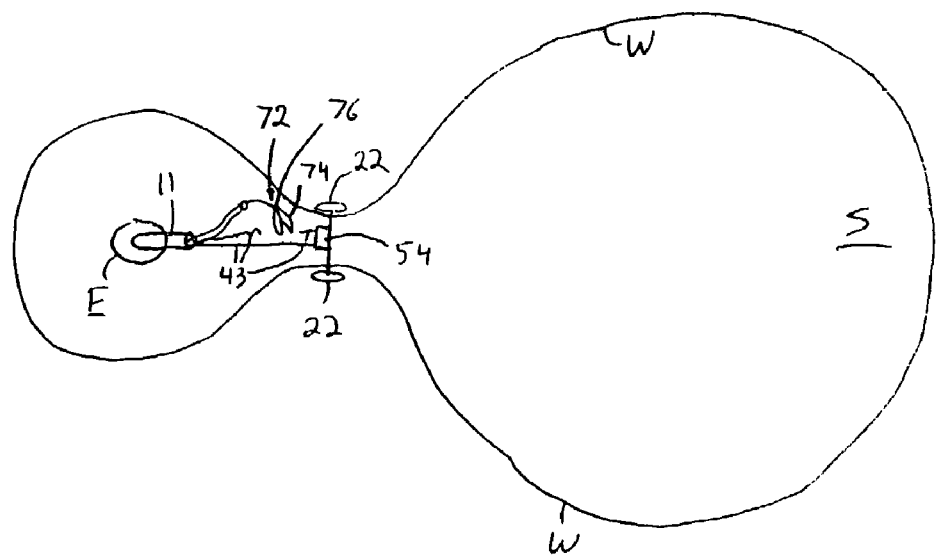

FIG. 8H depicts a step in which scissors assembly 72 is used to cut unneeded lengths of sutures 43 after fastener 54 has been crimped. Scissors assembly 72 comprises blades 74 arranged to articulate about pivot point 76. Scissor assembly 72 is manipulated into cutting position and used to cut the sutures using an actuator disposed generally at the proximal end of catheter 11. Once sutures 43 have been cut, the excess length of sutures 43 is removed through the patient's mouth and scissor assembly 72 is retracted through delivery catheter 11. Advantageously, narrowing of stomach S limits the amount of food the patient consumes by providing a feeling of satiety after only a small amount of food is ingested.

Figure 9A:
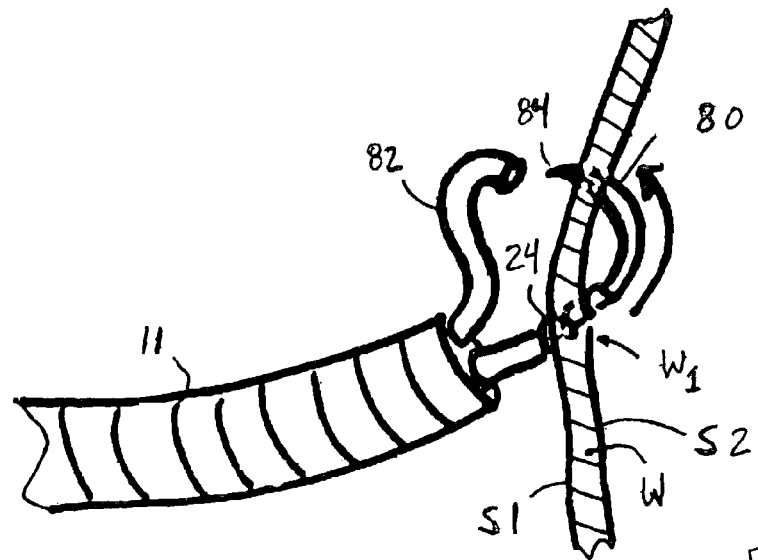
FIGS. 9A-9C are perspective views of an alternative delivery catheter featuring a curved needle according to the present invention.
Figure 9B:
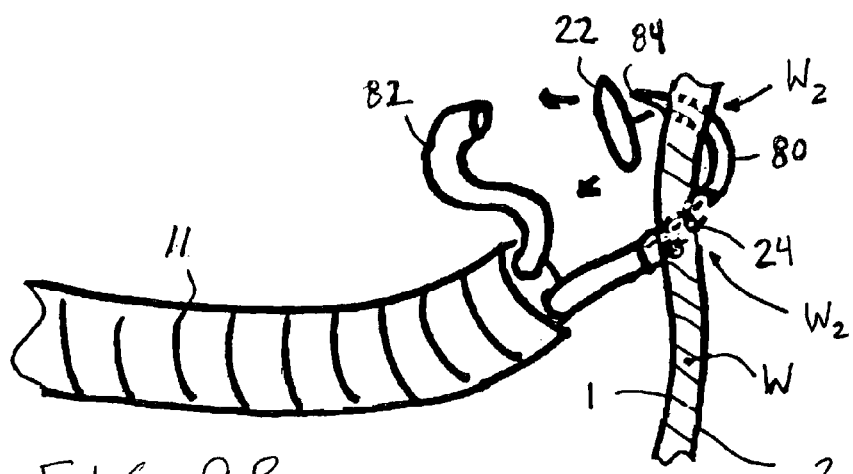
Figure 9C:
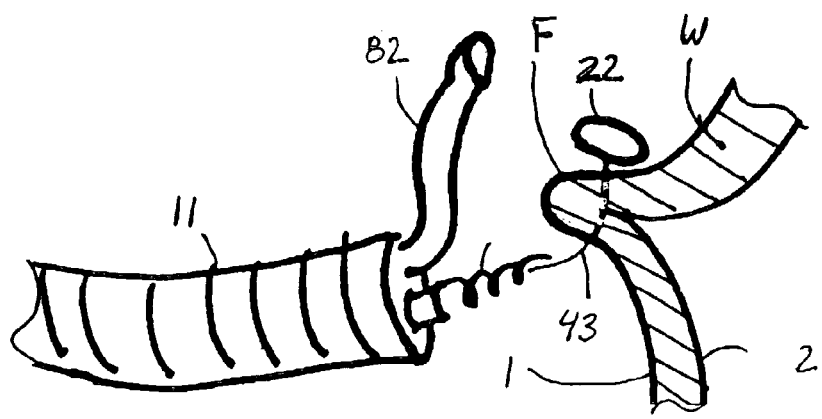

Referring to FIGS. 9A-9C, a method of creating a gastrointestinal tissue fold will now be described. The initial step involves providing delivery catheter 11 comprising coil screw 24 and a translatable curved needle 80. In addition, endoscope 82 may be provided to visualize the site and aid in anchor delivery. Referring to FIG. 9A, once coil screw 24 has been screwed into tissue wall W, curved needle 80 is deployed through coil screw 24 such that needle 80 penetrates tissue wall W at first location W1. As needle 80 is deployed from the distal tip of catheter 11, it curves outwardly such that full deployment results in the needle curving around and penetrating tissue wall W at second location W2. In other words, initial deployment of needle 80 through coil screw 24 causes the needle to penetrate tissue wall (at W1) such that distal tip 84 of the needle moves from first side S1 of the tissue wall to second side S1 of the tissue wall.

Further deployment of needle 80 through coil screw 24 causes the needle to penetrate the tissue wall for a second time (at W2) such that distal tip 152 moves from the second side of the tissue wall back to the first side of the tissue wall. Referring to FIG. 9B, anchor assembly 22 is ejected through the needle after distal tip 84 penetrates the tissue wall for the second time. After ejecting anchor assembly 22, the needle is retracted. Referring to FIG. 9C, tensioning of the suture 43 produces fold F in tissue wall W between first location W1 and second location W2.

Referring now to FIGS. 10A-10D, an alternative method of creating a gastrointestinal tissue fold will now be described. The initial step involves providing a delivery catheter 11 comprising translatable needle 16 and deployable jaw assembly 90. Delivery catheter 11 also may include an endoscope to visualize the site and aid in anchor delivery.

Figure 10A:
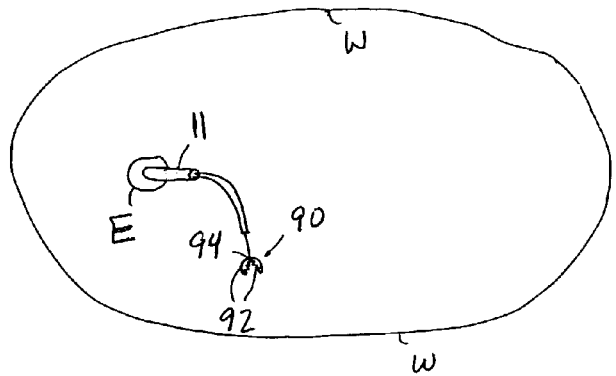
FIGS. 10A-10D are cross-sectional views depicting another method of forming a gastrointestinal fold according to the present invention.
Figure 10B:
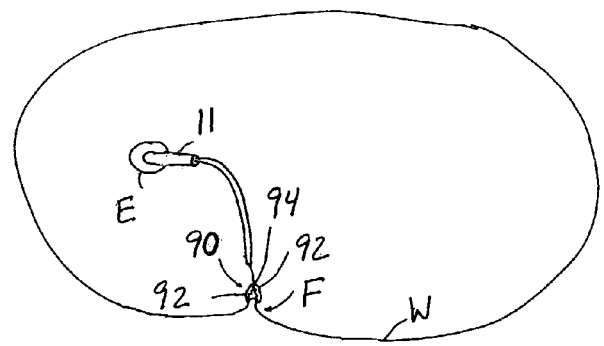

Jaw assembly 90 comprises pair of jaws 92 arranged to rotate about pivot point 94. FIG. 10A depicts a step in which jaw assembly 90 is deployed and articulated into a position adjacent tissue wall W using an actuator disposed generally at the proximal end of delivery catheter 11. FIG. 10B depicts a step in which jaw assembly 90 is used to grab and pull tissue wall W to create fold F. The creation of fold F facilitates the penetration of tissue wall W by needle 16 and subsequent delivery of anchor assembly 22.

Figure 10C:
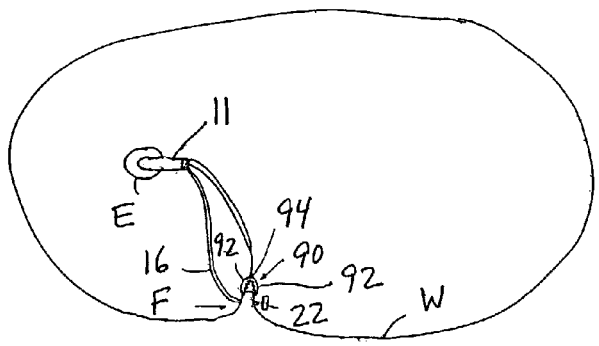
Figure 10D:
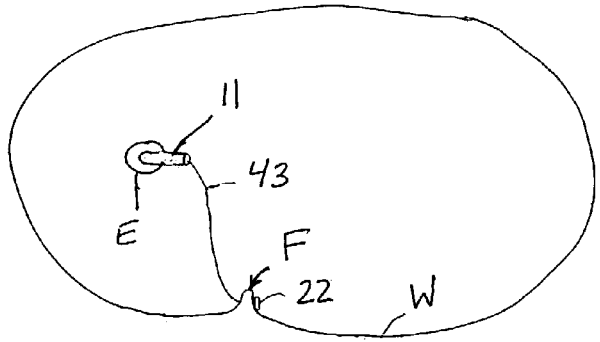

FIG. 10C depicts a step in which needle 16 is deployed and articulated such that the needle tip penetrates through fold F created using jaw assembly 90. After the needle tip passes through fold F, anchor assembly 22 is ejected. FIG. 10D depicts a step in which jaw assembly 90 and needle 16 are retracted into delivery catheter 11. Suture 43 extends from anchor 22 through tissue fold F and into delivery catheter 11; the tissue fold is maintained by applying tension to suture 43. The foregoing steps to create a gastrointestinal tissue fold may be repeated to create additional tissue folds. These tissue folds may be approximated by applying tension to the sutures and then tying the sutures together or, alternatively, using a fastener 54 such as described with respect to FIG. 6.

The anchors of the present invention may be ejected through a tissue wall or a tissue fold. By applying tension to the sutures, the tissue walls or tissue folds engaging the anchors are pulled into proximity with each other.

Figure 11:
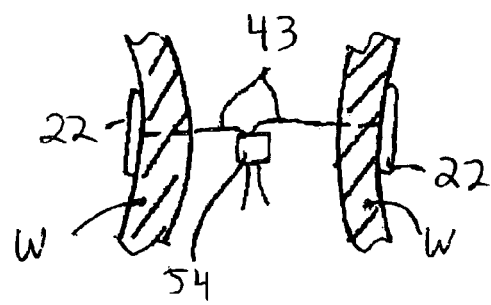
FIGS. 11-14 are side-sectional views of alternative methods of the present invention for approximating gastrointestinal tissue.
Figure 12:
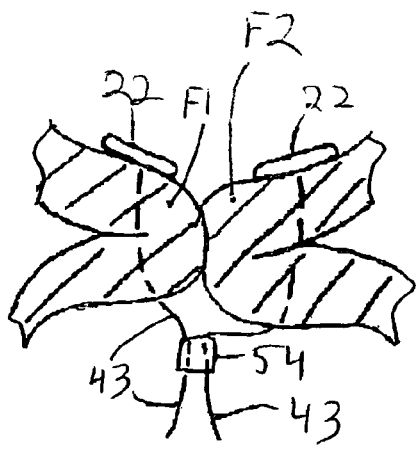

FIGS. 11-14 depict various methods of approximating gastrointestinal tissue walls w and/or tissue folds F. More particularly, FIG. 11 depicts the approximation of a pair of tissue walls W. After anchors 22 have been delivered (e.g., as disclosed with respect to FIGS. 1-3) and walls W are approximated and fastener 43 then is crimped to hold the walls in the approximated position. FIG. 12 depicts the approximation of a pair of folds F1, F2 that are disposed on opposing tissue walls. After anchors 22 have been delivered (e.g., as disclosed with respect to FIGS. 9A-9C or 10A-10D) and folds F1, F2 are approximated, fastener 43 is crimped to hold the folds in the approximated position.

Figure 13:
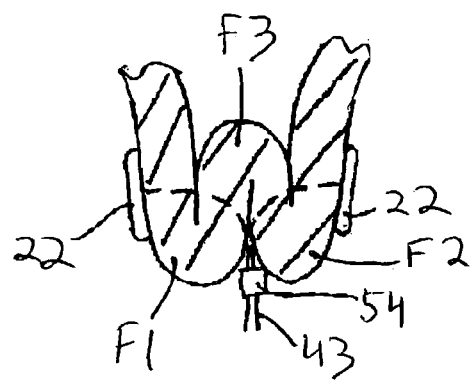
Figure 14:
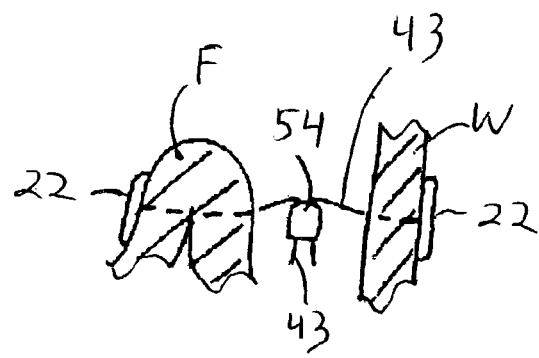

FIG. 13 depicts the approximation of a pair of folds F1, F2 that are disposed adjacent to each other on tissue wall. Anchors 22 again may be delivered as disclosed with respect to FIGS. 9A-9C or 10A-10D. However, the approximation of adjacent folds F1, F2 creates a third fold F3 disposed generally between folds F1, F2 and oriented in a substantially opposite direction. The combination of folds F1, F2, F3 form a W-shape, as depicted in FIG. 13. After approximation, fastener 43 is crimped to hold the folds in the approximated position. FIG. 14 depicts the approximation of fold F and tissue wall W. Anchor 22a can be delivered as disclosed with respect to FIGS. 1-3 and anchor 22b may be delivered as disclosed with respect to FIGS. 9A-9C or 10A-10D. After anchor delivery, fold F and tissue wall W are approximated and fastener 54 is crimped to hold the fold and tissue wall in the approximated position.

Figure 15:
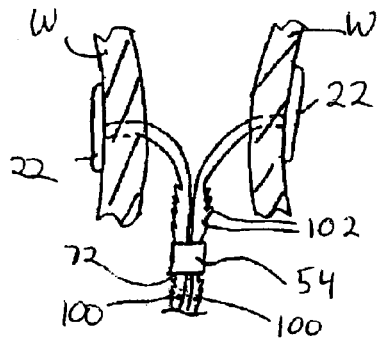
FIG. 15 is a side-sectional view of teethed suture suitable for use with the fastener of FIG. 6.
Figure 16:
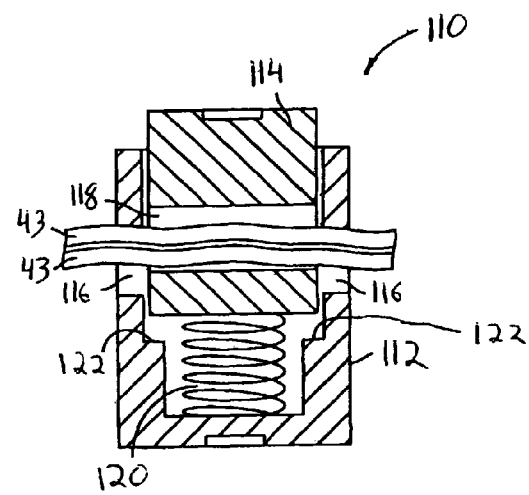
FIG. 16 is a cross-sectional view of an alternative fastener of the present invention.

Referring to FIG. 15, teethed suture 100 configured for use with fastener 54 (as described with respect to FIG. 6) will now be described. As depicted in FIG. 15, a pair of anchors 22 including teethed sutures 100 have been delivered through opposing tissue walls W of a gastrointestinal lumen. Each teethed suture 100 comprises a polymeric or metal strand having teeth 102 partially disposed along the length of teethed suture 100. Teethed sutures 100 are configured to be inserted simultaneously through fastener channel 72 in a first direction such that they may not be pulled back through channel 72 in the opposite direction. Accordingly, teethed sutures 100 may be inserted through the channel, but teeth 102 do not allow the teethed sutures to be pulled back through channel 72 because the teeth engage the fastener lip along the outer periphery of channel 72.

FIG. 15 depicts adjustable clip 110 suitable for use as a suture fastener in lieu of fastener 54 (as described with respect to FIG. 6). Adjustable clip 110 comprises housing 112 and engagement piece 114 translatably disposed within housing 112. Housing 112 has bore 116, which is disposed orthogonal to the direction of translation of engagement piece 114, and has a cross-sectional area that accommodates unrestricted movement of sutures 43 therebetween. Engagement piece 114 has bore 118 disposed substantially parallel to bore 116 with a cross-sectional area that also accommodates unrestricted movement of sutures 43 therebetween.

Adjustable clip 110 further comprises spring 120 disposed between housing 112 and engagement piece 114 to bias engagement piece 114 so that the bores 116, 118 are misaligned absent an external force that counters the force of spring 120. When the bores 116, 118 are misaligned, sutures 43 are constrained from freely translating therebetween. However, when an external force is applied to counter the biasing force of spring 120, engagement piece 114 translates within housing 112 until engagement piece 144 contacts ledge 122. At this point, bores 116, 118 are aligned such that sutures 43 may freely translate therebetween, thus permitting the suture tension to be adjusted. Advantageously, this permits the overall reduction in the cross-section area of the gastrointestinal lumen to be readily adjusted.

Figure 17A:
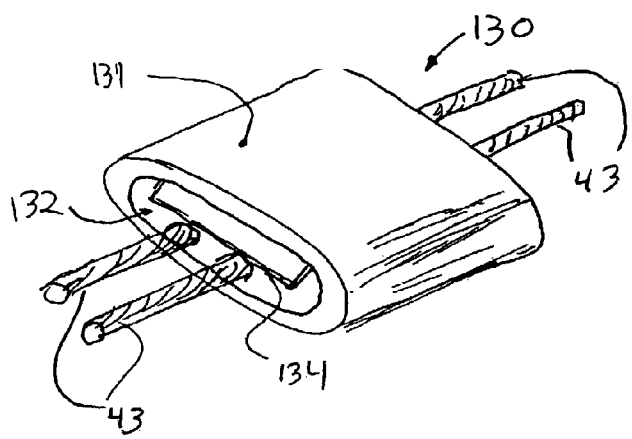
FIGS. 17A and 17E are, respectively, perspective and cross-sectional views of further alternative fasteners constructed in accordance with the principles of the present invention.

FIG. 17A depicts alternative fastener 130 that may be used to maintain the tension in one or more sutures 43 after tissue approximation. Fastener 130 includes housing 131 and channel 132 within which suture 43 may pass freely. One end of channel 132 includes sharpened edge or blade 134 which may be positioned at least partially around the perimeter of channel 132 such that crimping fastener 130 causes blade 134 to extend into channel 132 and sever sutures 43 that extend beyond blade 134.

Figure 17B:
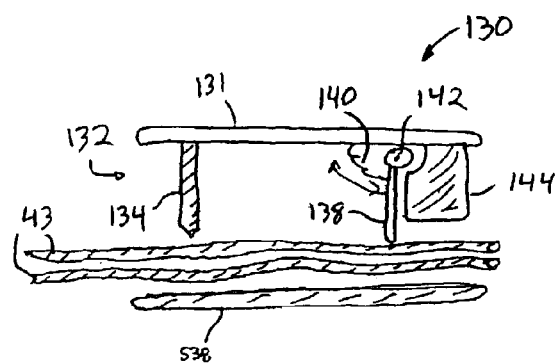

Although fastener 130 may be configured to allow sutures 43 to pass freely therebetween, fastener 130 is preferably designed to permit unidirectional travel of sutures 43 through the fastener. This allows sutures 43 to be tightened through the anchors but prevents sutures 43 from slipping back and releasing the tension within the anchors. FIGS. 17B-17E show various alternative designs which allow for unidirectional tensioning of sutures 43. More particularly, FIG. 17B shows a cross-sectional side view of one variation of fastener 130 in which tension is maintained within sutures 43 via ratchet 138. As fastener 130 is passed over sutures 43 through channel 132, ratchet 138 allows sutures 43 to pass freely yet remains in contact due to the biasing force of spring element 140. However, when sutures 43 slip in the opposite direction, ratchet 138 rotates about pivot 142 and is stopped by stop 144. The edge of ratchet 138 engages sutures 43 to stop movement of sutures 43 in the reverse direction. After sutures 43 have been tightened, fastener 130 may be crimped so that blade 134 is urged against sutures 43 and severs them from the deployed anchors.

Figure 17C:
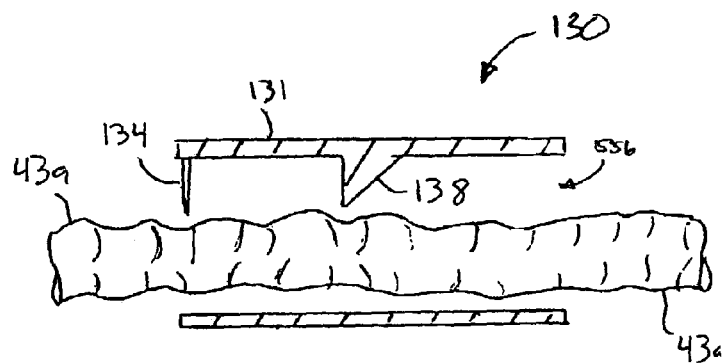

FIG. 17C depicts another alternative fastener 130, wherein ratchet 138 is formed integrally with fastener 130 and coarse suture 43a is employed to present a roughened surface for ratchet 138. As suture 43a is passed through the fastener channel, the angle of ratchet 138 allows for the unidirectional travel of suture 43a from right to left. If pulled in the opposite direction, ratchet 138 engages the roughened surface and prevents movement of suture 43a in the reverse direction. After suture 43a has been desirably tensioned, fastener 130 may be crimped to sever suture 43a with blade 134.

Figure 17D:
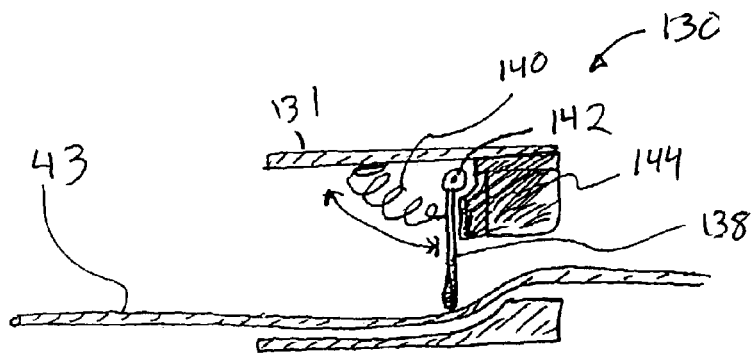
Figure 17E:
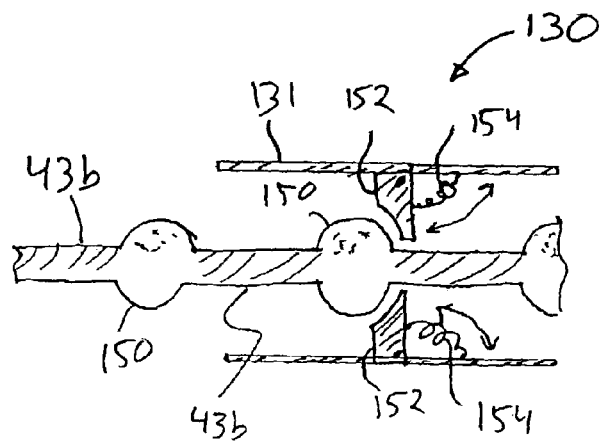

FIG. 17D depicts a further alternative fastener 130, wherein ratchet 138 is rotatable about pivot 142 while remaining in contact with suture 43 due to the biasing force of spring element 140. The rotation of ratchet 138 is limited by stop 144, which enables ratchet 138 to press suture 43 against housing 131, thereby stopping the movement of fastener 130 relative to suture 43. FIG. 17E depicts yet another alternative fastener 130 that utilizes roughened or beaded suture 43b. Suture 43b preferably defines a plurality of beads or knots 150 periodically along its length. Ratchet 138 is configured such that it may open in one direction, thereby allowing the passage of suture 43b, yet movement of suture 43b in the opposite direction forces ratchet 152 to close due to biasing spring element 154. Ratchet 152 is preferably configured such that suture 43b may pass through in the reverse direction, but because of beads or knots 150, further slippage of suture 43b is prevented.

Although preferred illustrative embodiments of the present invention are described above, it will be evident to one skilled in the art that various changes and modifications may be made without departing from the invention. It is intended in the appended claims to cover all such changes and modifications that fall within the true spirit and scope of the invention.

What is claimed is:

1. A method for delivering an anchor for use in a gastric reduction system for reducing the cross-sectional area of a gastrointestinal lumen, comprising:
   providing a delivery catheter having a needle translatably disposed therein, a distal end, a stabilization device disposed at the distal end and one or more anchors disposed within the needle, with at least one of the anchors comprising a sleeve of braided material and an eyelet for attaching the anchor to a suture;
   advancing the delivery catheter into the gastrointestinal lumen;
   engaging the stabilization device to a tissue wall of the gastrointestinal lumen;
   advancing the needle through the tissue wall;
   ejecting an anchor from a distal tip of the needle, the anchor having a suture attached thereto;
   withdrawing the needle from the tissue wall whereby the suture is extended through the tissue wall; and
   translating a fastener over the suture whereby a tension force is created on the suture and a tissue fold is maintained in the tissue wall.

2. The method of claim 1, further comprising: providing an imaging element in the vicinity of the distal end of the delivery catheter; and using the imaging element to provide visual guidance during engagement of the stabilization device to the tissue wall.

3. The method of claim 1, wherein ejecting an anchor from a distal tip of the needle comprises translating a push rod disposed in the needle.

4. The method of claim 1, wherein the stabilization device comprises a coil having a sharpened tip, and engaging the stabilization device to the tissue wall comprises rotating the coil to engage the coil into the tissue wall.

5. The method of claim 1, wherein advancing the needle through the tissue wall further comprises translating the needle distally through the delivery catheter.

6. A method comprising:
providing a delivery catheter including a piercing element within the catheter, one or more anchors within the catheter and a suture coupled to the anchors, with at least one of the anchors comprising a sleeve of braided material and an eyelet for coupling the anchor to the suture;
advancing the delivery catheter into the gastrointestinal tract of a patient;
advancing the piercing element through a first tissue wall, and then through a second tissue wall;
ejecting a first anchor from the piercing element on a first side of the first tissue wall, and ejecting a second anchor from the piercing element on a second side of the second tissue wall; and
advancing a fastener over the suture whereby a tension is applied to the suture, the fastener comprising a collar having a central channel through which the suture extends;
such that the first and second anchors and the suture hold the first tissue wall adjacent to the second tissue wall.

7. The method of claim 6, further comprising:
providing a stabilization device on the delivery catheter; and engaging the stabilization device to the first tissue wall before advancing the catheter through the first tissue wall.

8. The method of claim 7, wherein the stabilization device comprises a tissue holding element.

9. The method of claim 6, further comprising: providing an imaging element in the vicinity of the distal end of the delivery catheter; and using the imaging element to provide visual guidance.

10. The method of claim 6 wherein bringing the first and second tissue walls adjacent results in reducing the cross sectional area of an opening in the patient.

11. The method of claim 6 wherein bringing the first and second tissue walls adjacent results in reducing the volume of an organ of the patient.

12. A method for creating a gastrointestinal tissue fold, comprising:
providing a delivery catheter having a translatable needle and an anchor disposed within the needle and a suture coupled to the anchor, the anchor comprising a sleeve of braided material and an eyelet for coupling the anchor to a suture;
engaging and pulling a tissue wall of the gastrointestinal lumen to create a tissue fold;
extending the needle through the tissue fold;
ejecting the anchor from the needle;
withdrawing the needle from the tissue fold whereby the suture is extended through the tissue fold;
translating a fastener over the suture; and
maintaining the tissue fold via the anchor and the suture.

13. The method of claim 12, further comprising: providing a second anchor including a suture coupled thereto; and creating a second tissue fold on an opposing tissue wall.

14. A method comprising:
moving a catheter into a patient;
holding a tissue fold within the patient;
extending a piercing element from the catheter through the tissue fold;
moving a first anchor out from the piercing element, on a first side of the tissue fold;
withdrawing the piercing element from the tissue fold;
moving a second anchor out from the piercing element, on a second side of the tissue fold, with at least one of the first anchor and the second anchor comprising a sleeve of braided material and an eyelet for coupling the anchor to a connection element;
holding the tissue fold via a connection element connecting the first and second anchors; and
advancing a fastener over said connection element to apply a tension force on said connection element.

15. The method of claim 14 wherein forming the tissue fold results in reducing the cross sectional area of a lumen in the patient.

16. The method of claim 14 wherein forming the tissue fold reduces the volume of an organ in the patient.

17. A method of creating a tissue fold comprising:
moving a catheter to a surgical site of a patient;
engaging and pulling a tissue wall to form a tissue fold;
pushing a piercing element extending out of the catheter through the tissue fold;
ejecting a first anchor from the piercing element;
withdrawing the piercing element from the tissue fold;
ejecting a second anchor from the piercing element, said second anchor being connected to said first anchor by a suture, with at least one of the first anchor and the second anchor comprising a sleeve of braided material and an eyelet for coupling the anchor to the suture; and
advancing a fastener over said suture to apply a tension force on said suture;
with the anchors and the suture maintaining the tissue fold.

18. A method comprising:
providing a system having a delivery catheter having a translatable needle and anchors disposed within the needle, and a suture coupled to the anchors, with at least one of the anchors comprising a sleeve of braided material and an eyelet for coupling the anchor to the suture;
engaging and pulling a tissue wall of the gastrointestinal tract of a patient to create a tissue fold;
extending the needle through the tissue fold;
placing an anchor on one side of the tissue fold;
releasing the tissue fold;
placing an anchor on the opposite side of the tissue fold, with the anchors connected to each other via the suture; and
advancing a fastener over said suture to apply a tension force on said suture;
with the anchors and suture maintaining the tissue fold after the tissue fold is released.

19. A method comprising:
moving a catheter into a patient;
holding a tissue fold within the patient;
extending a piercing element from the catheter through the tissue fold;
moving a first anchor out from the piercing element, on a first side of the tissue fold;
withdrawing the piercing element from the tissue fold;
moving a second anchor out from the piercing element, on a second side of the tissue fold, with at least one of the first anchor and the second anchor comprising a sleeve of braided material and an eyelet for coupling the anchor to a connection element; and
holding the tissue fold via a connection element connecting the first and second anchors.

20. A method comprising:
moving a catheter having a tissue grasper and a piercing element into a patient;
holding a tissue fold within the patient with the tissue grasper;

extending the piercing element from the catheter through the tissue fold;

moving a first anchor out from the piercing element, on a first side of the tissue fold;

withdrawing the piercing element from the tissue fold;

moving a second anchor out from the piercing element, on a second side of the tissue fold, with at least one of the first anchor and the second anchor comprising a sleeve of braided material and an eyelet for coupling the anchor to a connection element; and holding the tissue fold via a connection element connecting the first and second anchors.

* * * * *